United States Patent [19]
Reed et al.

[11] Patent Number: 5,912,166
[45] Date of Patent: Jun. 15, 1999

[54] COMPOUNDS AND METHODS FOR DIAGNOSIS OF LEISHMANIASIS

[75] Inventors: Steven G. Reed, Bellevue, Wash.; Yasir A. W. Skeiky, Seattle, Wash.

[73] Assignee: Corixa Corporation, Seattle, Wash.

[21] Appl. No.: 08/428,414

[22] Filed: Apr. 21, 1995

[51] Int. Cl.$^6$ .......................... C12N 15/00; G01N 33/53; C07K 5/00; C07K 16/00
[52] U.S. Cl. ................ 435/320.1; 435/7.1; 435/7.22; 435/7.92; 435/7.95; 435/975; 530/300; 530/326; 530/388.1; 530/387.1; 530/388.6; 530/387.9; 530/810; 530/822
[58] Field of Search .................. 530/300, 326, 530/388.1, 387.1, 388.6, 387.9, 810, 822; 435/7.1, 7.22, 7.92, 320.1, 7.95, 975

[56] References Cited

U.S. PATENT DOCUMENTS

| | | |
|---|---|---|
| 4,992,273 | 2/1991 | Monjour et al. |
| 5,304,371 | 4/1994 | Reed ......................................... 424/88 |
| 5,411,865 | 5/1995 | Reed . |
| 5,719,263 | 2/1998 | Reed . |

FOREIGN PATENT DOCUMENTS

| | | | |
|---|---|---|---|
| 293 827 A2 | 12/1988 | European Pat. Off. ..... | G01N 33/569 |
| WO 89/01045 | 2/1989 | WIPO ............................. | C12P 21/00 |
| WO 93/16199 | 8/1993 | WIPO . | |
| 9416331 | 7/1994 | WIPO . | |

OTHER PUBLICATIONS

Skeiky et al., "Antigens Shared by *Leishmania* Species and *Trypanosoma cruzi*: Immunological Comparison of the Acidic Ribosomal P0 Proteins," *Infection and Immunity* 62(5): 1643–1651, (1994).

Burns, Jr. et al., "Molecular chaacterization of a kinesin–related antigen of *Leishmania chagasi* that detects specific antibody in African and American visceral leishmaniasis," *Proc. Natl. Acad. Sci. USA* 90: 775–779, 1993.

Skeiky et al., "Cloning and Expression of *Trypanosoma cruzi* Ribosomal Protein P0 and Epitode Analysis of Anti–P0 Autoantibodies in Chagas' Disease Patients," *Journal of Experimental Medicine* 176 : 201–211, 1992.

Soto et al., "Isolation, characterization and analysis of the expression of the *Leishmania* ribosomal P0 protein genes," *Molecular and Biomedical Parasitology 61*: 265–274, 1993.

Soto et al., "Genomic Organization and Expression of Two Independent Gene Arrays Coding for Two Antigenic Acidic Ribosomal Proteins of *Leishmania*," *Journal of Biological Chemistry* 268(29): 21835–21843, 1993.

Jeronimo et al, Trans. Royal Soc. Trop. Med & Hyg. 88/4:386–388, 1994.

Vinhas et al, Brazilian J. Med. Biol. Res. 27:1199–1205, 1994.

White et al, Am. J. Trop. Med. Hyg. 46/2: 123–131, 1992.

Reed et al. 1987. J. Immunol. 138(5): 1596–601.

Reed et al. 1990. Am. J. Trop. Med. Hyg. 43(6):632–39.

Dillon et al. 1995, PNAS (USA). 92: 7981–85.

Bowie et al, Science, 247:1306–1310 1990.

Bixler et al. In. Synthetic Vaccines vol. 1:39–71 1987.

*Primary Examiner*—Nita Minnifield
*Attorney, Agent, or Firm*—Seed and Berry LLP

[57] ABSTRACT

Compounds and methods are provided for diagnosing Leishmania infection. Disclosed compounds include polypeptides that contain at least an epitope of the *Leishmania chagasi* acidic ribosomal antigen LcP0, or a variant thereof. Such compounds are useful in a variety of immunoassays for detecting Leishmania infection and for identifying individuals with asymptomatic infections that are likely to progress to acute visceral leishmaniasis. The polypeptide compounds are further useful in vaccines and pharmaceutical compositions for preventing leishmaniasis.

24 Claims, 18 Drawing Sheets

```
ATAGCCAAGG CTATTGCAAG TCTCACAAG ATG CCG TCT ATC ACC ACT GCC AAG        53
                                Met Pro Ser Ile Thr Thr Ala Lys
                                 1               5
CGC GAG TAC GAG GAG CGC CTC GTC GAC TGC CTG ACC AAG TAC AGC TGC       101
Arg Glu Tyr Glu Glu Arg Leu Val Asp Cys Leu Thr Lys Tyr Ser Cys
         10              15                  20
GTG CTG TTC GTG GGC ATG GAC AAC GTC CGC TCG CAG CAG GTG CAC GAT       149
Val Leu Phe Val Gly Met Asp Asn Val Arg Ser Gln Gln Val His Asp
 25              30                  35                      40
GTG CGC CGT GGC TGT CGC GGC AAG GCC GAG TTC ATT ATG GGC AAG AAG       197
Val Arg Arg Gly Cys Arg Gly Lys Ala Glu Phe Ile Met Gly Lys Lys
                 45                  50                  55
ACG CTG CAG GCG AAG ATC GTG GAG AAG CGC GCG CAA GCC AAG GAC GCG       245
Thr Leu Gln Ala Lys Ile Val Glu Lys Arg Ala Gln Ala Lys Asp Ala
             60                  65                  70
AGC CCC GAG GCG AAG CCT TTC AAC GAT CAG TGT GAG GAG TAC AAC CTG       293
Ser Pro Glu Ala Lys Pro Phe Asn Asp Gln Cys Glu Glu Tyr Asn Leu
         75                  80                  85
CTG AGC GGC AAC ACC GGC CTC ATC TTC ACT AAC AAC GCT GTC CAG GAG       341
Leu Ser Gly Asn Thr Gly Leu Ile Phe Thr Asn Asn Ala Val Gln Glu
         90                  95                 100
ATC ACC TCT GTG CTT GAC GGC CAC CGC GTG AAG GCC CCG GCG CGT GTC       389
Ile Thr Ser Val Leu Asp Gly His Arg Val Lys Ala Pro Ala Arg Val
105                 110                 115                 120
GGA GCG ATT CCG TGC GAC GTG GTT GTG CCT GCT GGC AGC ACC GGC ATG       437
Gly Ala Ile Pro Cys Asp Val Val Val Pro Ala Gly Ser Thr Gly Met
                125                 130                 135
GAG CCG ACC CAG ACG TCC TTC TTC CAG GCG CTG AAC ATT GCG ACG AAG       485
Glu Pro Thr Gln Thr Ser Phe Phe Gln Ala Leu Asn Ile Ala Thr Lys
             140                 145                 150
ATT GCC AAG GGT ATG GTG GAG ATC GTG ACG GAG AAG AAG GTG CTG AGC       533
Ile Ala Lys Gly Met Val Glu Ile Val Thr Glu Lys Lys Val Leu Ser
             155                 160                 165
GTC GGC GAC AAG GTG GAC AAC TCG ACG GCG ACG CTG CTG CAA AAG CTG       581
Val Gly Asp Lys Val Asp Asn Ser Thr Ala Thr Leu Leu Gln Lys Leu
         170                 175                 180
AAC ATC AGC CCG TTC TAC TAC CAG GTG AAT GTG CTG TCC GTG TGG GAC       629
Asn Ile Ser Pro Phe Tyr Tyr Gln Val Asn Val Leu Ser Val Trp Asp
185                 190                 195                 200
CGC GGT GTG CTG TTC ACC CGC GAG GAC CTC ATG ATG ACG GAG GAC ATG       677
Arg Gly Val Leu Phe Thr Arg Glu Asp Leu Met Met Thr Glu Asp Met
                205                 210                 215
GTG GAG AAG ATG CTG ATG GAA GGC CTG AGC AAC GTT GCG GCG ATG GCG       725
Val Glu Lys Met Leu Met Glu Gly Leu Ser Asn Val Ala Ala Met Ala
             220                 225                 230
CTG GGT GCT GGC ATC CCG ACG TCT TCG ACG ATT GGC CCG ATG CTG GTG       773
Leu Gly Ala Gly Ile Pro Thr Ser Ser Thr Ile Gly Pro Met Leu Val
             235                 240                 245
```

*Fig. 1A*

```
GAC GCC TTC AAG AAC CTG CTG GCT GTC TCC GTG GCG ACC TCG TAC GAG        821
Asp Ala Phe Lys Asn Leu Leu Ala Val Ser Val Ala Thr Ser Tyr Glu
    250                 255                 260
TTC GAG GAG CAC AAC GGC AAG GAG CTG CGC GAG GCC GCG ATC AAC GGC        869
Phe Glu Glu His Asn Gly Lys Glu Leu Arg Glu Ala Ala Ile Asn Gly
265                 270                 275                 280
CTG CTG GCC GGC TCT GGC TCG GCT GCT GCG GAG CCC GCC GCT GCC GCG        917
Leu Leu Ala Gly Ser Gly Ser Ala Ala Ala Glu Pro Ala Ala Ala Ala
                285                 290                 295
CCG GCC GCC CCT AGC GCT GCT GCC AAG GAG GAG CCG GAG GAG AGC GAC        965
Pro Ala Ala Pro Ser Ala Ala Ala Lys Glu Glu Pro Glu Glu Ser Asp
                300                 305                 310
GAG GAC GAC TTC GGC ATG GGC GGT CTC TTC TAA GCGACTCGCT ATCCGCCACC     1018
Glu Asp Asp Phe Gly Met Gly Gly Leu Phe  *
                315                 320
CAGCACCGTC GAGTGTTCGT GCGTTCGCAT GGTGGACAGT GGCGAGCGTG TGATGCCCTT     1078
GGATCATCAG GAAGCAACTC TCTCCCTTTC TCTGGGTGTT CTTCGTTTCT TCTTTCATTT     1138
GTTTTTGATC GCCGTGGCGC TGCGGCGATC GCTCAGTTCT TATTTTCGAT CAACCAACAA     1198
CGAA                                                                 1202
```

*Fig. 1B*

```
Met His Pro Ser Thr Val Arg Arg Glu Ala Glu Arg Val Lys Val Ser
1             5                   10                  15
Val Arg Val Arg Pro Leu Asn Glu Arg Glu Asn Asn Ala Pro Glu Gly
            20                  25                  30
Thr Lys Val Thr Val Ala Ala Lys Gln Ala Ala Ala Val Val Thr Val
            35                  40                  45
Lys Val Leu Gly Gly Ser Asn Asn Ser Gly Ala Ala Glu Ser Met Gly
    50                  55                  60
Thr Ala Arg Arg Val Ala Gln Asp Phe Gln Phe Asp His Val Phe Trp
65              70                  75                      80
Ser Val Glu Thr Pro Asp Ala Cys Gly Ala Thr Pro Ala Thr Gln Ala
            85                  90                  95
Asp Val Phe Arg Thr Ile Gly Tyr Pro Leu Val Gln His Ala Phe Asp
            100                 105                 110
Gly Phe Asn Ser Cys Leu Phe Ala Tyr Gly Gln Thr Gly Ser Gly Lys
            115                 120                 125
Thr Tyr Thr Met Met Gly Ala Asp Val Ser Ala Leu Ser Gly Glu Gly
    130                 135                 140
Asn Gly Val Thr Pro Arg Ile Cys Leu Glu Ile Phe Ala Arg Lys Ala
145             150                 155                 160
Ser Val Glu Ala Gln Gly His Ser Arg Trp Ile Val Glu Leu Gly Tyr
            165                 170                 175
Val Glu Val Tyr Asn Glu Arg Val Ser Asp Leu Leu Gly Lys Arg Lys
            180                 185                 190
Lys Gly Val Lys Gly Gly Glu Glu Val Tyr Val Asp Val Arg Glu
    195                 200                 205
His Pro Ser Arg Gly Val Phe Leu Glu Gly Gln Arg Leu Val Glu Val
    210                 215                 220
Gly Ser Leu Asp Asp Val Val Arg Leu Ile Glu Ile Gly Asn Gly Val
225                 230                 235                 240
Arg His Thr Ala Ser Thr Lys Met Asn Asp Arg Ser Ser Arg Ser His
            245                 250                 255
Ala Ile Ile Met Leu Leu Leu Arg Glu Glu Arg Thr Met Thr Thr Lys
            260                 265                 270
Ser Gly Glu Thr Ile Arg Thr Ala Gly Lys Ser Ser Arg Met Asn Leu
    275                 280                 285
Val Asp Leu Ala Gly Ser Glu Arg Val Ala Gln Ser Gln Val Glu Gly
    290                 295                 300
Gln Gln Phe Lys Glu Ala Thr His Ile Asn Leu Ser Leu Thr Thr Leu
305             310                 315                 320
Gly Arg Val Ile Asp Val Leu Ala Asp Met Ala Thr Lys Gly Ala Lys
            325                 330                 335
```

*Fig. 2A*

Ala Gln Tyr Ser Val Ala Pro Phe Arg Asp Ser Lys Leu Thr Phe Ile
                340                 345                 350
Leu Lys Asp Ser Leu Gly Gly Asn Ser Lys Thr Phe Met Ile Ala Thr
                355                 360                 365
Val Ser Pro Ser Ala Leu Asn Tyr Glu Glu Thr Leu Ser Thr Leu Arg
            370                 375                 380
Tyr Ala Ser Arg Ala Arg Asp Ile Val Asn Val Ala Gln Val Asn Glu
385                 390                 395                 400
Asp Pro Arg Ala Arg Arg Ile Arg Glu Leu Glu Glu Gln Met Glu Asp
                405                 410                 415
Met Arg Gln Ala Met Ala Gly Gly Asp Pro Ala Tyr Val Ser Glu Leu
                420                 425                 430
Lys Lys Lys Leu Ala Leu Leu Glu Ser Glu Ala Gln Lys Arg Ala Ala
                435                 440                 445
Asp Leu Gln Ala Leu Glu Arg Glu Arg Glu His Asn Gln Val Gln Glu
            450                 455                 460
Arg Leu Leu Arg Ala Thr Glu Ala Glu Lys Ser Glu Leu Glu Ser Arg
465                 470                 475                 480
Ala Ala Ala Leu Gln Glu Glu Met Thr Ala Thr Arg Arg Gln Ala Asp
                485                 490                 495
Lys Met Gln Ala Leu Asn Leu Arg Leu Lys Glu Gln Ala Arg Lys
                500                 505                 510
Glu Arg Glu Leu Leu Lys Glu Met Ala Lys Lys Asp Ala Ala Leu Ser
                515                 520                 525
Lys Val Arg Arg Arg Leu Asp Ala Glu Ile Ala Ser Glu Arg Glu Lys
            530                 535                 540
Leu Glu Ser Thr Val Ala Gln Leu Glu Arg Glu Gln Arg Glu Arg Glu
545                 550                 555                 560
Val Ala Leu Asp Ala Leu Gln Thr His Gln Arg Lys Leu Gln Glu Ala
                565                 570                 575
Leu Glu Ser Ser Glu Arg Thr Ala Ala Glu Arg Asp Gln Leu Leu Gln
                580                 585                 590
Gln Leu Thr Glu Leu Gln Ser Glu Arg Thr Gln Leu Ser Gln Val Val
            595                 600                 605
Thr Asp Arg Glu Arg Leu Thr Arg Asp Leu Gln Arg Ile Gln Tyr Glu
            610                 615                 620
Tyr Gly Glu Thr Glu Leu Ala Arg Asp Val Ala Leu Cys Ala Ala Gln
625                 630                 635                 640
Glu Met Glu Ala Arg Tyr His Ala Ala Val Phe His Leu Gln Thr Leu
                645                 650                 655
Leu Glu Leu Ala Thr Glu Trp Glu Asp Ala Leu Arg Glu Arg Ala Leu
            660                 665                 670
Ala Glu Arg Asp Glu Ala Ala Ala Glu Leu Asp Ala Ala Ser
            675                 680                 685

*Fig. 2B*

```
Thr Ser Gln Asn Ala Arg Glu Ser Ala Cys Glu Arg Leu Thr Ser Leu
    690             695             700
Glu Gln Gln Leu Arg Glu Ser Glu Glu Arg Ala Ala Glu Leu Ala Ser
705             710             715             720
Gln Leu Glu Ala Thr Ala Ala Ala Lys Ser Ser Ala Glu Gln Asp Arg
            725             730             735
Glu Asn Thr Arg Ala Thr Leu Glu Gln Gln Leu Arg Glu Ser Glu Ala
            740             745             750
Arg Ala Ala Glu Leu Ala Ser Gln Leu Glu Ala Thr Ala Ala Ala Lys
            755             760             765
Met Ser Ala Glu Gln Asp Arg Glu Asn Thr Arg Ala Thr Leu Glu Gln
770             775             780
Gln Leu Arg Asp Ser Glu Glu Arg Ala Ala Glu Leu Ala Ser Gln Leu
785             790             795             800
Glu Ser Thr Thr Ala Ala Lys Met Ser Ala Glu Gln Asp Arg Glu Ser
            805             810             815
Thr Arg Ala Thr Leu Glu Gln Gln Leu Arg Asp Ser Glu Glu Arg Ala
            820             825             830
Ala Glu Leu Ala Ser Gln Leu Glu Ser Thr Thr Ala Ala Lys Met Ser
            835             840             845
Ala Glu Gln Asp Arg Glu Ser Thr Arg Ala Thr Leu Glu Gln Gln Leu
            850             855             860
Arg Glu Ser Glu Glu Arg Ala Ala Glu Leu Ala Ser Gln Leu Glu Ser
865             870             875             880
Thr Thr Ala Ala Lys Met Ser Ala Glu Gln Asp Arg Glu Ser Thr Arg
            885             890             895
Ala Thr Leu Glu Gln Gln Leu Arg Asp Ser Glu Glu Arg Ala Ala Glu
            900             905             910
Leu Ala Ser Gln Leu Glu Ala Thr Ala Ala Lys Ser Ser Ala Glu
            915             920             925
Gln Asp Arg Glu Asn Thr Arg Ala Ala Leu Glu Gln Gln Leu Arg Asp
    930             935             940
Ser Glu Glu Arg Ala Ala Glu Leu Ala Ser Gln
945             950             955
```

*Fig. 2C*

```
GCTCCCACGG CGCTACCCCC TTTCCCGCAT GTGCGACAGT TTCACGCGTA CAAACGTCTT    60
TCTCTCTCCT TCGCGCGTGT CGCTATGGGC GGCGGCGCGT CGGTGTCTTT GATTGCACAG   120
CTCACCGCCT CGCCATATTT TCGTCGTGGC CACGCGACCC CCCGACCTTC CCCTCCTCCG   180
CCCCCAAAGA CAAGCCAGAC ATACCGACCA TGCCGTCTGC CCGCGTCTCT GCTTACCAAG   240
CGCGCCACGC ACCCCTTCCT CGGCCCTGAA TCTTTCGCGC GGCGCCATAC ATTGCATGCA   300
CGTCACTACG CCTGTACACC TTACACCTCC TCTTGCCCAC CCCTTTCCCC TTCTACACGC   360
CTAACTACAC ACACATATAT ATATATATAT ATAAAGCGCT CAACGCACAC ATACTGTGGC   420
CAGTATTACT GCACCAACGT CTGCCTCTTC CAGGATGCAC CCTTCCACTG TGCGGCGTGA   480
GGCGGAGCGG GTGAAGGTGT CGGTGCGCGT GCGCCCCCTA AACGAACGTG AAAACAATGC   540
CCCGGAAGGG ACGAAAGTGA CCGTTGCGGC GAAACAGGCG GCCGCCGTGG TGACGGTCAA   600
GGTCCTGGGA GGCAGCAACA ACAGCGGCGC CGCCGAGTCG ATGGGGACTG CAAGGCGGGT   660
AGCGCAGGAC TTTCAGTTCG ACCACGTGTT CTGGTCTGTG GAGACGCCGG ACGCGTGCGG   720
CGCGACCCCC GCGACGCAGG CAGACGTGTT CCGGACGATC GGGTACCCGC TGGTGCAGCA   780
CGCGTTCGAC GGGTTCAACT CGTGCTTGTT TGCGTACGGG CAGACAGGGA GCGGGAAGAC   840
GTACACGATG ATGGGCGCGG ACGTGAGCGC GCTTAGTGGT GAGGGCAACG GCGTGACGCC   900
GCGGATCTGC CTGGAGATCT TTGCGCGGAA GGCGAGCGTG GAGGCGCAGG GGCACTCGCG   960
GTGGATCGTG GAGCTGGGGT ACGTGGAGGT GTACAACGAG CGCGTGTCGG ACCTGCTTGG  1020
GAAGCGGAAG AAGGGTGTGA AGGGCGGCGG CGAGGAGGTG TACGTGGACG TGCGCGAGCA  1080
CCCGAGCCGC GGCGTGTTCC TGGAGGGGCA GCGGCTGGTG GAGGTTGGGA GCCTGGACGA  1140
TGTTGTGCGG CTGATCGAGA TCGGCAACGG CGTGCGGCAC ACCGCTTCGA CGAAGATGAA  1200
CGACCGGAGC AGCCGGAGCC ACGCGATCAT CATGCTGCTG CTGCGCGAGG AGCGGACGAT  1260
GACGACGAAG AGCGGGGAGA CGATCCGTAC TGCCGGCAAG AGCAGCCGCA TGAACCTTGT  1320
GGACCTTGCG GGGTCTGAGC GCGTGGCGCA GTCGCAGGTG GAGGGGCAGC AGTTCAAGGA  1380
GGCGACGCAC ATCAACCTGT CGCTGACGAC GCTCGGGCGC GTGATCGACG TGCTCGCGGA  1440
CATGGCGACG AAGGGTGCGA AGGCGCAGTA CAGCGTTGCG CCGTTCCGCG ACTCGAAGCT  1500
GACGTTCATC CTGAAGGACT CGCTTGGCGG GAACTCGAAG ACGTTCATGA TCGCGACTGT  1560
GAGCCCGAGC GCGCTGAACT ACGAGGAGAC GCTGAGCACG CTGCGGTACG CGTCGCGCGC  1620
GCGCGACATT GTGAATGTTG CGCAGGTGAA CGAGGACCCG CGCGCACGGC GGATCCGCGA  1680
GCTGGAGGAG CAGATGGAGG ACATGCGGCA GGCGATGGCT GGCGGCGACC CCGCGTACGT  1740
GTCTGAGCTG AAGAAGAAGC TTGCGCTGCT GGAGTCGGAG GCGCAGAAGC GTGCGGCGGA  1800
CCTGCAGGCG CTGGAGAGGG AGCGGGAGCA CAACCAGGTG CAGGAGCGGC TGCTGCGCGC  1860
GACGGAGGCG GAGAAGAGCG AGCTGGAGTC GCGTGCGGCT GCGCTGCAGG AGGAGATGAC  1920
```

*Fig. 3A*

```
CGCGACTCGA CGGCAGGCGG ACAAGATGCA GGCGCTGAAC CTGCGGCTGA AGGAAGAGCA    1980
GGCGCGCAAG GAGCGCGAGC TGCTGAAAGA GATGGCGAAG AAGGACGCCG CGCTCTCGAA    2040
GGTTCGGCGA CGCAAAGACG CCGAGATAGC AAGCGAGCGC GAGAAGCTGG AGTCGACCGT    2100
GGCGCAGCTG GAGCGTGAGC AGCGCGAGCG CGAGGTGGCT CTGGACGCAT GCAGACGCA    2160
CCAGAGAAAG CTGCAGGAAG CGCTCGAGAG CTCTGAGCGG ACAGCCGCGG AAAGGGACCA    2220
GCTGCTGCAG CAGCTAACAG AGCTTCAGTC TGAGCGTACG CAGCTATCAC AGGTTGTGAC    2280
CGACCGCGAG CGGCTTACAC GCGACTTGCA GCGTATTCAG TACGAGTACG GGGAAACCGA    2340
GCTCGCGCGA GACGTGGCGC TGTGCGCCGC GCAGGAGATG GAGGCGCGCT ACCACGCTGC    2400
TGTGTTTCAC CTGCAAACGC TCCTGGAGCT CGCAACCGAG TGGGAGGACG CACTCCGCGA    2460
GCGTGCGCTT GCAGAGCGTG ACGAAGCCGC TGCAGCCGAA CTTGATGCCG CAGCCTCTAC    2520
TTCCCAAAAC GCACGTGAAA GCGCCTGCGA GCGGCTAACC AGCCTTGAGC AGCAGCTTCG    2580
CGAATCCGAG GAGCGCGCTG CGGAGCTGGC GAGCCAGCTG GAGGCCACTG CTGCTGCGAA    2640
GTCGTCGGCG GAGCAGGACC GCGAGAACAC GAGGGCCACG CTAGAGCAGC AGCTTCGCGA    2700
ATCCGAGGCG CGCGCTGCGG AGCTGGCGAG CCAGCTGGAG GCCACTGCTG CTGCGAAGAT    2760
GTCAGCGGAG CAGGACCGCG AGAACACGAG GCCACGCTA GAGCAGCAGC TTCGTGACTC    2820
CGAGGAGCGC GCTGCGGAGC TGGCGAGCCA GCTGGAGTCC ACTACTGCTG CGAAGATGTC    2880
AGCGGAGCAG GACCGCGAGA GCACGAGGGC CACGCTAGAG CAGCAGCTTC GTGACTCCGA    2940
GGAGCGCGCT GCGGAGCTGG CGAGCCAGCT GGAGTCCACT ACTGCTGCGA AGATGTCAGC    3000
GGAGCAGGAC CGCGAGAGCA CGAGGGCCAC GCTAGAGCAG CAGCTTCGCG AATCCGAGGA    3060
GCGCGCTGCG GAGCTGGCGA GCCAGCTGGA GTCCACTACT GCTGCGAAGA TGTCAGCGGA    3120
GCAGGACCGC GAGAGCACGA GGGCCACGCT AGAGCAGCAG CTTCGTGACT CCGAGGAGCG    3180
CGCTGCGGAG CTGGCGAGCC AGCTGGAGGC CACTGCTGCT GCGAAGTCGT CGGCGGAGCA    3240
GGACCGCGAG AACACGAGGG CCGCGTTGGA GCAGCAGCTT CGTGACTCCG AGGAGCGCGC    3300
CGCGGAGCTG GCGAGCCAG                                                  3319
```

*Fig. 3B*

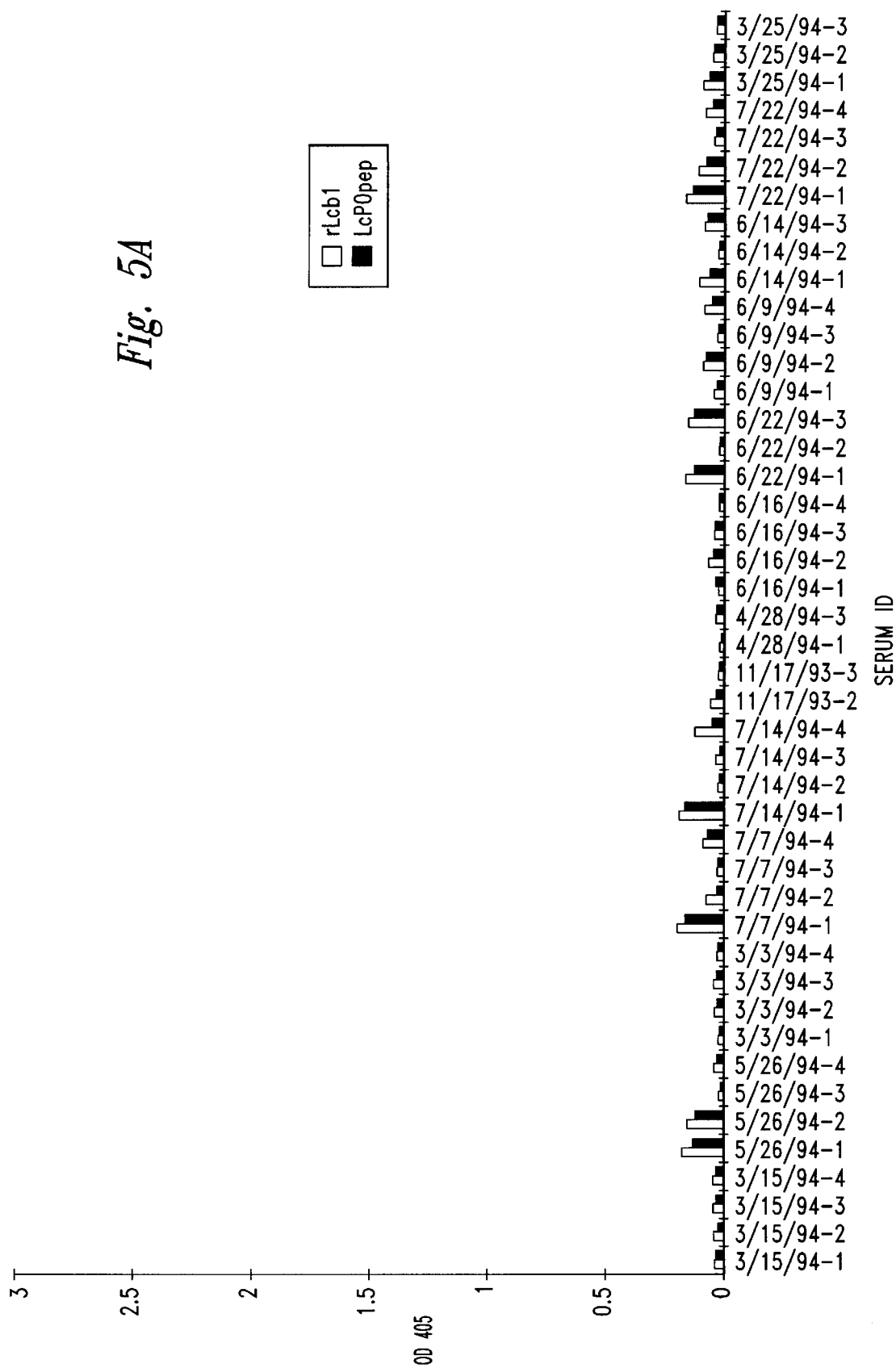

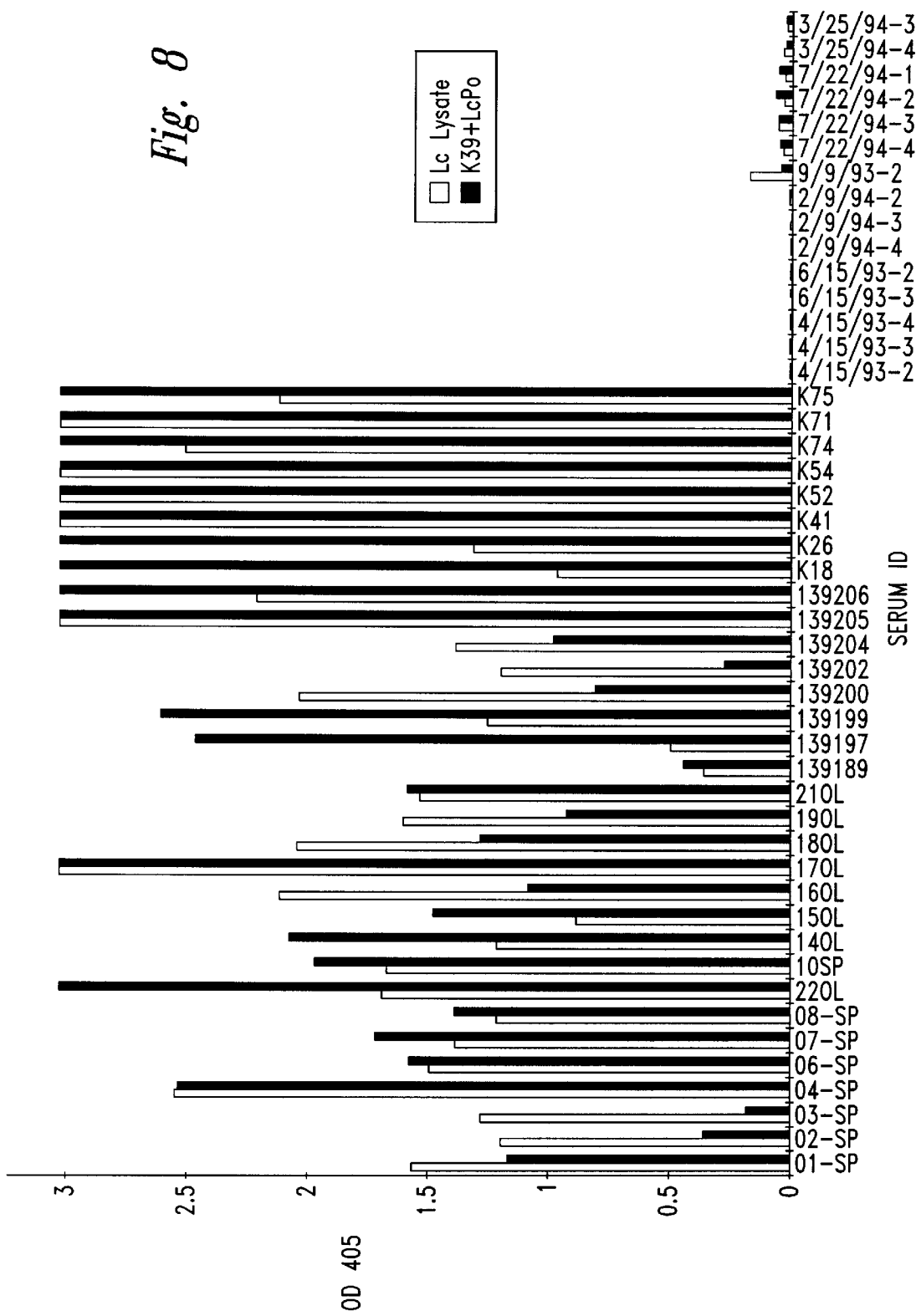

COMPOUNDS AND METHODS FOR DIAGNOSIS OF LEISHMANIASIS

TECHNICAL FIELD

The present invention relates generally to the serodiagnosis of Leishmania infection. The invention is more particularly directed to the use of one or more Leishmania polypeptides in methods and diagnostic kits to screen individuals and blood supplies for Leishmania, and to identify those asymptomatic individuals that are likely to progress to acute visceral leishmaniasis. The invention is also directed to vaccines and pharmaceutical compositions for immunizing an individual against leishmaniasis.

BACKGROUND OF THE INVENTION

Leishmania organisms are intracellular protozoan parasites of macrophages that cause a wide range of clinical diseases in humans and other animals. In some infections, the parasite may lie dormant, and an infected host may be asymptomatic for many years. In other cases, particularly in immunocompromised individuals, the host may develop one of a variety of forms of leishmaniasis. This disease may be subclinical visceral leishmaniasis (VL) or asymptomatic in nature. Patients with subclinical or asymptomatic disease usually have low antibody titers which fall into the gray zone in immunological tests using whole parasites or parasite lysates. Isolation of parasites from these patients is also extremely difficult. Subclinical patients will in some cases progress to acute disease, but often will self-heal. They exhibit mild symptoms of malaise, diarrhea and intermittent hepatomegaly. Asymptomatic patients, in addition to low antibody titers, also display strong, positive delayed hypersensitivity to leishmanial antigens. Alternatively, leishmaniasis may be manifested as a cutaneous disease, which is a severe medical problem but is generally self-limiting, or as a highly destructive mucosal disease. Finally, and most seriously, the disease may be manifested as an acute visceral infection involving the spleen, liver, and lymph nodes, which is generally a fatal disease. Symptoms of acute visceral leishmaniasis include hepatosplenomegaly, fever, leukopenia, anemia and hypergammaglobulinemia.

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis (VL).

There are 20 species of Leishmania that infect humans. Of these species, VL is generally caused by L. donovani in Africa, China, the Middle East and India, L. infantium in southern Europe and North Africa, or L. chagasi in Latin America. In general, Leishmania species are transmitted to humans and other mammals, primarily the dog, by the bite of a phlebotomine sand fly.

Early diagnosis of leishmaniasis is crucial for successful treatment, but is difficult to achieve with existing techniques. There are no distinctive signs or symptoms of the disease. Parasite detection methods have been used, but such methods are not sensitive or practical. Current serological tests (using, for example, ELISA or immunofluorescence techniques) typically use whole or lysed parasites, and are generally insensitive and prone to cross-reaction with a variety of other diseases. Such methods often fail to detect the potentially fatal disease early enough to allow effective treatment, since they rely on the detection of antibodies that are present during the acute phase of the disease.

Accordingly, there is a need in the art for more sensitive and specific methods for detecting Leishmania infection, and for identifying those asymptomatic Leishmania infections that are likely to progress to acute visceral infections. The present invention fulfills these needs and further provides other related advantages.

SUMMARY OF THE INVENTION

Briefly stated, this invention provides compounds and methods for detecting and protecting against leishmaniasis in individuals and in blood supplies. In one aspect, the present invention provides methods for detecting asymptomatic or sub-clinical Leishmania infection in a biological sample, comprising: (a) contacting a biological sample with a polypeptide comprising an epitope of LcP0, or a variant thereof that differs only in conservative substitutions and/or modifications; and (b) detecting in the biological sample the presence of antibodies that bind to the polypeptide, thereby detecting asymptomatic or subclinical Leishmania infection in the biological sample.

In a related aspect, the present invention provides methods for detecting Leishmania infection in a biological sample, comprising: (a) contacting a biological sample with a first amino acid sequence comprising an epitope of LcP0, or a variant thereof that differs only in conservative substitutions and/or modifications; (b) contacting the biological sample with a second amino acid sequence comprising Leu Glu Gln Gln Leu Arg Xaa Ser Glu Xaa Arg Ala Ala Glu Leu Ala Ser Gln Leu Glu Xaa Thr Xaa Ala Ala Lys Xaa Ser Ala Glu Gln Asp Arg Glu Xaa Thr Arg Ala Xaa, wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala, (SEQ ID NO:5) or a variant thereof that differs only in conservative substitutions and/or modifications; and (c) detecting in the sample the presence of antibodies that bind to one or both of the amino acid sequences, thereby detecting Leishmania infection in the biological sample.

In yet another related aspect of this invention, methods are provided for identifying a patient afflicted with asymptomatic or subclinical leishmaniasis that is likely to develop acute visceral leishmaniasis. In one embodiment, the method comprises: (a) contacting a biological sample obtained from a patient afflicted with asymptomatic or subclinical leishmaniasis with a polypeptide comprising the amino acid sequence Leu Glu Gln Gln Leu Arg Xaa Ser Glu Xaa Arg Ala Ala Glu Leu Ala Ser Gln Leu Glu Xaa Thr Xaa Ala Ala Lys Xaa Ser Ala Glu Gln Asp Arg Glu Xaa Thr Arg Ala Xaa, wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala, (SEQ ID NO:5) or a variant thereof that differs only in conservative substitutions and/or modifications; and (b) detecting in the sample the presence of antibodies that bind to the polypeptide, thereby identifying a patient afflicted with asymptomatic or subclinical leishmaniasis that is likely to develop acute visceral leishmaniasis.

In another embodiment, the method comprises: (a) contacting a biological sample obtained from a patient afflicted with asymptomatic or subclinical leishmaniasis with a first polypeptide comprising an epitope of LcP0, or a variant thereof that differs only in conservative substitutions and/or modifications; (b) independently contacting the biological sample with a second polypeptide comprising the amino acid sequence Leu Glu Gin Gln Leu Arg Xaa Ser Glu Xaa Arg Ala Ala Glu Leu Ala Ser Gin Leu Glu Xaa Thr Xaa Ala Ala Lys Xaa Ser Ala Glu Gln Asp Arg Glu Xaa Thr Arg Ala Xaa, wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala, (SEQ ID NO:5) or a variant thereof that differs only in conservative substitutions and/or modifications; and (c) detecting in the sample the presence of antibodies that bind to the first and/or second polypeptides, thereby identifying a patient afflicted with asymptomatic or subclinical leishmaniasis that is likely to develop acute visceral leishmaniasis.

In another aspect of this invention, polypeptides are provided comprising amino acids 306–322 of SEQ ID NO:2.

Within related aspects, diagnostic kits for diagnosing leishmaniasis are provided. In one embodiment, this invention provides kits for detecting asymptomatic or sub-clinical leishmaniasis in a biological sample, comprising: (a) a polypeptide comprising an epitope of LcP0, or a variant thereof that differs only in conservative substitutions and/or modifications; and (b) a detection reagent.

In another embodiment, diagnostic kits are provided for detecting Leishmania infection in a biological sample, comprising: (a) a first amino acid sequence comprising an epitope of LcP0, or a variant thereof that differs only in conservative substitutions and/or modifications; (b) a second amino acid sequence comprising the amino acid sequence Leu Glu Gln Gin Leu Arg Xaa Ser Glu Xaa Arg Ala Ala Glu Leu Ala Ser Gin Leu Glu Xaa Thr Xaa Ala Ala Lys Xaa Ser Ala Glu Gin Asp Arg Glu Xaa Thr Arg Ala Xaa, wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala, (SEQ ID NO:5) or a variant thereof that differs only in conservative substitutions and/or modifications; and (c) a detection reagent.

In still another embodiment, diagnostic kits are provided for identifying a patient afflicted with asymptomatic or subclinical leishmaniasis that is likely to develop acute visceral leishmaniasis, comprising: (a) a polypeptide comprising the amino acid sequence Leu Glu Gin Gin Leu Arg Xaa Ser Glu Xaa Arg Ala Ala Glu Leu Ala Ser Gin Leu Glu Xaa Thr Xaa Ala Ala Lys Xaa Ser Ala Glu Gln Asp Arg Glu Xaa Thr Arg Ala Xaa, wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala, (SEQ ID NO:5) or a variant thereof that differs only in conservative substitutions and/or modifications; and (b) a detection reagent.

In yet another related embodiment, the present invention provides diagnostic kits for identifying a patient afflicted with asymptomatic or subclinical leishmaniasis that is likely to develop acute visceral leishmaniasis, comprising: (a) a first polypeptide comprising an epitope of LcP0, or a variant thereof that differs only in conservative substitutions and/or modifications; (b) a second polypeptide comprising the amino acid sequence Leu Glu Gln Gin Leu Arg Xaa Ser Glu Xaa Arg Ala Ala Glu Leu Ala Ser Gln Leu Glu Xaa Thr Xaa Ala Ala Lys Xaa Ser Ala Glu Gin Asp Arg Glu Xaa Thr Arg Ala Xaa, wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala, (SEQ ID NO:5) or a variant thereof that differs only in conservative substitutions and/or modifications; and (c) a detection reagent.

Within other aspects, this invention provides pharmaceutical compositions comprising a polypeptide containing an epitope of LcP0, or a variant thereof that differs only in conservative substitutions and/or modifications, and a physiologically acceptable carrier; and vaccines comprising a polypeptide as described above and an adjuvant.

In related aspects, DNA sequences encoding the above polypeptides, expression vectors comprising these DNA sequences and host cells transformed or transfected with such expression vectors are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1(a) and (b) show the sequence of a representative cDNA molecule encoding LcP0, along with the amino acid sequence encoded by the cDNA.

FIGS. 2(a), (b), and (c) depict the sequence of the full length K39 polypeptide.

FIGS. 3(a) and (b) present the DNA sequence of a representative cDNA encoding the full length K39 polypeptide.

FIG. 4 illustrates the reactivity of LcP0.

FIG. 5 illustrates the reactivity of a polypeptide containing the 17 C-terminal amino acids of LcP0 as compared to that of recombinant LcP0. FIG. 5(a) shows the reactivity with sera from normal individuals.

FIG. 6 shows the reactivity of the 17 amino acid polypeptide evaluated in FIG. 5.

FIG. 7 illustrates the reactivity of the recombinant K39 polypeptide.

FIG. 8 shows the reactivity of LcP0 together with K39, as compared to that of Leishmania lysate, with sera from normal, asymptomatic and visceral leishmaniasis patients.

DESCRIPTION OF THE INVENTION

Figure 4A:
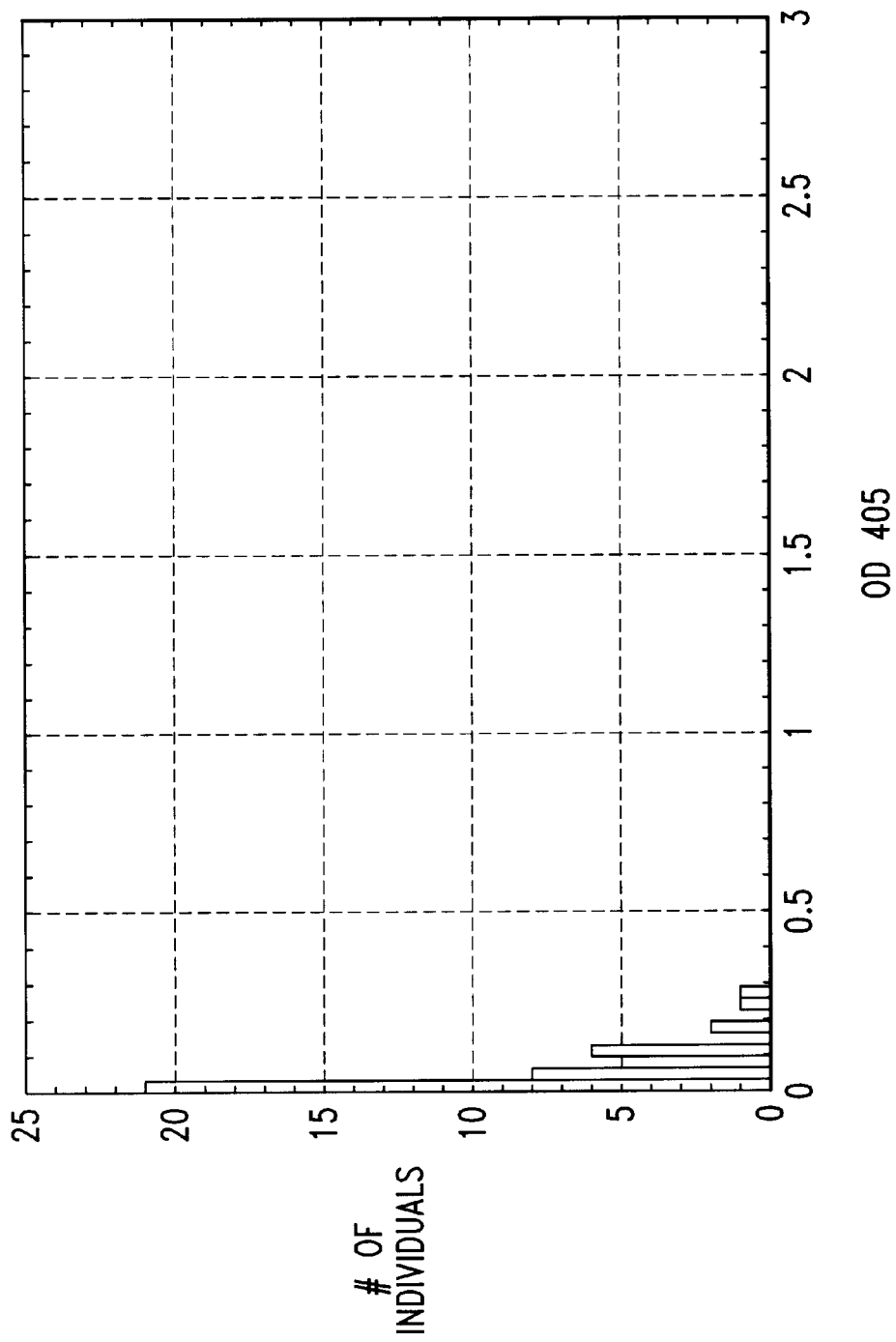
FIG. 4(a) shows the reactivity with sera from normal individuals.

As noted above, the present invention is generally directed to compounds and methods useful for detecting and protecting against Leishmania infection. The compounds of this invention generally comprise one or more antigenic epitopes of Leishmania proteins. In particular, polypeptides comprising an epitope of a *Leishmania chagasi* homolog of the eukaryotic acidic ribosomal P-protein family (referred to herein as LcP0) are disclosed. As used herein, the term "polypeptide" encompasses amino acid chains of any length, including full length proteins, wherein the amino acid residues are linked by covalent peptide bonds. The use of such LcP0 polypeptides for specifically detecting asymptomatic or subclinical leishmaniasis is also disclosed. In addition, the present invention discloses the use of epitopes from other Leishmania proteins, in combination with an epitope of LcP0, to diagnose Leishmania infection and to monitor the development of acute visceral leishmaniasis.

The compounds and methods of this invention also encompass variants of the recited polypeptides. As used herein, a "variant" is a polypeptide that differs from the recited polypeptide only in conservative substitutions and/or modifications, such that it retains the antigenic properties of the recited polypeptide. Such variants may generally be identified by modifying the polypeptide sequence as described below and evaluating the antigenic properties of the modified polypeptide using, for example, one or more of the assays described herein. A "conservative substitution" in the context of this invention is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. Preferred substitutions include changes between asp and glu, ala and glu, ala and ser, ala and thr, met and ser, and asn and ser. Variants may also, or alternatively, contain other modifications, including the deletion or addition of amino acids, that have minimal influence on the antigenic properties, secondary structure and hydropathic nature of the polypeptide. For example, the polypeptide may be conjugated to a linker or other sequence for ease of synthesis or to enhance binding of the polypeptide to a solid support.

In one aspect of the invention, polypeptides are provided comprising an epitope of the *Leishmania chagasi* acidic ribosomal antigen LcP0. A genomic DNA sequence encoding LcP0 is shown in FIGS. 1 (*a*) and (*b*). A DNA molecule encoding LcP0 may be isolated by screening a *Leishmania chagasi* genomic expression library for clones that express antigens which react with pooled sera from *T. cruzi*-infected patients. This screen may be generally performed using methods known to those of ordinary skill in the art, such as methods described in Sambrook et al., *Molecular Cloning. A Laboratory Manual*, Cold Spring Harbor Laboratories, Cold Spring Harbor, N.Y. 1989, which is incorporated herein by reference. Briefly, a bacteriophage expression library may be plated and transferred to filters. The filters may then be incubated with serum and a detection reagent. In the context of this invention, a "detection reagent" is any compound capable of binding to the antibody-antigen complex, which may then be detected by any of a variety of means known to those of ordinary skill in the art. Typical detection reagents contain a "binding agent," such as Protein A, Protein G, IgG or a lectin, coupled to a reporter group. Preferred reporter groups include, but are not limited to, enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenzthiazoline sulfonic acid. Plaques containing genomic DNA sequences that express a protein which binds to an antibody in the serum may be isolated and purified by techniques known to those of ordinary skill in the art. Appropriate methods may be found, for example, in Sambrook et al., *Molecular Cloning: A Laboratory Manual*, Cold Spring Harbor Laboratories, Cold Spring Harbor, N.Y.

Epitopes of LcP0 may generally be determined by generating polypeptides containing portions of the LcP0 sequence and evaluating the reactivity of the polypeptides with sera from Leishmania-infected individuals using, for example, an enzyme linked inimunosorbent assay (ELISA). Suitable assays for evaluating reactivity of a polypeptide with Leishmania-infected sera are described in more detail below. Within such representative assays, portions of the LcP0 sequence that generate a signal that differentiates between positive and negative sera in a manner substantially similar to that of the full length LcP0 are considered to contain an epitope. In other words, a portion of LcP0 that contains an epitope will generate a signal indicating Leishmania infection in substantially all (i.e., at least about 80%, and preferably at least about 90%) of the biological samples for which such infection would be indicated using the full length LcP0 and will generate a signal indicating the absence of Leishmania infection in substantially all of those samples that would be negative with the full length polypeptide. Portions of LcP0 containing at least the 17 C-terminal amino acids shown in FIGS. 1 (i.e., residues 306–322) have generally been found to generate a signal in an ELISA that is substantially equivalent to that generated by the full length LcP0. Accordingly, polypeptides comprising at least the 17 C-terminal amino acids of LcP0 contain an epitope of LcP0, and such polypeptides (and variants thereof) are within the scope of this invention.

In a related aspect, combination polypeptides comprising epitopes of multiple Leishmania polypeptides are disclosed. A "combination polypeptide" is a polypeptide in which epitopes of different Leishmania peptides, or variants thereof, are joined though a peptide linkage into a single amino acid chain. The epitopes may be joined directly (i.e., with no intervening amino acids) or may be joined by way of a linker sequence (e.g., Gly-Cys-Gly) that does not significantly alter the antigenic properties of the epitopes.

In preferred embodiments, the combination polypeptide comprises an LcP0 epitope along with an epitope derived from the Leishmania K39 antigen (see FIGS. 2(*a*), (*b*) and (*c*) and U.S. Pat. No. 5,411,865). More preferably, the K39 epitope is a K39 repeat unit antigen, having the amino acid sequence Leu Glu Gin Gin Leu Arg Xaa Ser Glu Xaa Arg Ala Ala Glu Leu Ala Ser Gin Leu Glu Xaa Thr Xaa Ala Ala Lys Xaa Ser Ala Glu Gin Asp Arg Glu Xaa Thr Arg Ala Xaa, wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala, (SEQ ID NO:5) or a variant thereof that differs only in conservative substitutions and/or modifications.

The polypeptides of this invention may be generated using techniques well known to those of ordinary skill in the art. Polypeptides having fewer than about 100 amino acids, and generally fewer than about 50 amino acids, can be synthesized using, for example, the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied Biosystems, Inc., Foster City, Calif. Thus, for example, the K39 repeat unit antigen, or portions thereof, may be synthesized by this method. Similarly, polypeptides comprising epitopes of LcP0, such as residues 306–322 of SEQ. ID NO:2, may be prepared using an automated synthesizer.

Alternatively, the polypeptides of this invention may be prepared by expression of recombinant DNA encoding the polypeptide in cultured host cells. Preferably, the host cells are *E. coli*, yeast, an insect cell line (such as Spodoptera or Trichoplusia) or a mammalian cell line, including (but not limited to) CHO, COS and NS-1. The DNA sequences expressed in this manner may encode naturally occurring proteins, such as LcP0 and K39, portions of naturally occurring proteins, or other variants of such proteins. Expressed polypeptides of this invention are generally isolated in substantially pure form. Preferably, the polypeptides are isolated to a purity of at least 80% by weight, more preferably, to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

In another aspect of this invention, methods are disclosed for detecting and monitoring Leishmania infection, as well as for distinguishing among types of Leishmania infections, in individuals and blood supplies. In general, Leishmania infection may be detected in any biological sample that contains antibodies. Preferably, the sample is blood, serum, plasma, saliva, cerebrospinal fluid or urine. More preferably, the sample is a blood or serum sample obtained from a patient or a blood supply. Briefly, Leishmania infection may be detected using one or more polypeptides containing one or more of the epitopes discussed above, or variants thereof. If multiple epitopes are employed, these epitopes may be present on one or more polypeptides. The polypeptide or polypeptides are then used to determine the presence or absence of antibodies to the polypeptide or polypeptides in the sample, relative to a predetermined cut-off value.

There are a variety of assay formats known to those of ordinary skill in the art for using a polypeptide to detect antibodies in a sample. See, e.g., Harlow and Lane, *Antibodies. A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that binds to the antibody/peptide complex and contains a detectable reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized polypeptide after incubation of the polypeptide with the sample. The extent to which components of the sample inhibit the binding of the labeled antibody to the polypeptide is indicative of the reactivity of the sample with the immobilized polypeptide.

The solid support may be any material known to those of ordinary skill in the art to which the polypeptide may be attached. For example, the support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptide may be bound to the solid support using a variety of techniques known to those in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen. Nitrocellulose will bind approximately 100 $\mu$g of protein per cm$^3$.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to a support having an appropriate polymer coating using benzoquinone or by condensation of an aldehyde group on the support with an amine and an active hydrogen on the polypeptide (see, e.g., Pierce Immunotechnology Catalog and Handbook (1991) at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

Once the polypeptide is immobilized on the support, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to permit detect the presence of antibody within a Leishmania-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibodypolypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g, Zymed Laboratories, San Francisco, Calif. and Pierce, Rockford, Ill.).

The detection reagent is then incubated with the immobilized antibodypolypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Leishmania antibodies in the sample, the signal detected from the reporter group that remains bound to the solid support is generally compared to a signal that corresponds to a predetermined cut-off value. In one preferred embodiment, the cut-off value is preferably the average mean signal obtained when the immobilized polypeptide is incubated with samples from an uninfected patient. In general, a sample generating a signal that is three standard deviations above the predetermined cut-off value is considered positive (i.e., reactive with the polypeptide). In an alternate preferred embodiment, the cut-off value is determined using a Receiver Operator Curve, according to the method of Sackett et al., *Clinical Epidemiology: A Basic Science for Clinical Medicine*, p. 106–7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper lefthand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In a related embodiment, the assay is performed in a flow-through or strip test format, wherein the antigen is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of Leishmania antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 µg, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only.

In one aspect of the invention, the assays discussed above may be used to specifically detect asymptomatic or subclinical leishmaniasis. In this aspect, antibodies in the sample may be detected using a polypeptide comprising LcP0 or an epitope thereof. Preferably, the polypeptide comprises amino acids 306–322 of SEQ ID NO:2. It has been found in the present invention that polypeptides comprising at least this C-terminal portion of LcP0 generate a positive result with sera from less than 35% of patients with acute visceral leishmaniasis, but generate a positive result with sera from more than 95% patients having asymptomatic or sub-clinical leishmaniasis. Accordingly, LcP0, and antigenic portions thereof, may be used to specifically identify patients with asymptomatic or sub-clinical leishmaniasis.

In another aspect, both asymptomatic/sub-clinical and acute visceral leishmaniasis may be detected. In this aspect, an LcP0 epitope is combined with a second Leishmania epitope that detects the presence of acute visceral leishmaniasis. Preferably, the second epitope comprises at least one repeat unit of the K39 antigen, the sequence of which is provided in FIGS. 2(a), (b) and (c) and SEQ ID NO:3. In one such embodiment, the K39 antigen comprises the repeat unit antigen having the amino acid sequence Leu Glu Gln Gln Leu Arg Xaa Ser Glu Xaa Arg Ala Glu Leu Ala Ser Gln Leu Glu Xaa Thr Xaa Ala Ala Lys Xaa Ser Ala Glu Gln Asp Arg Glu Xaa Thr Arg Ala Xaa, wherein Xaa at position 7 is Asp or Glu, at position 10 is Glu or Ala, at position 21 is Ala or Ser, at position 23 is Ala or Thr, at position 27 is Met or Ser, at position 35 is Asn or Ser, and at position 39 is Thr or Ala (SEQ ID NO:5). In another such preferred embodiment, the K39 epitope is present within a recombinant K39 polypeptide, which comprises amino acids 1-955 of SEQ ID NO:3. The use of variants of the above sequences, that differ only in conservative substitutions and/or modifications, is also preferred.

Preferably, the LcP0 and K39 antigens are immobilized by adsorption to a solid support such as a well of a microtiter plate or a membrane, as described above, in roughly similar amounts such that the total amount of polypeptide in contact with the support ranges from about 10 ng to about 100 µg. The remainder of the steps in the assay may generally be performed as described above. It will be readily apparent to those of ordinary skill in the art that, by combining LcP0 and K39 polypeptides with other polypeptides that can detect cutaneous and mucosal leishmaniasis, the polypeptides disclosed herein may be used in methods that detect all types of leishmaniasis.

In another aspect of the invention, patients with asymptomatic or subclinical VL whose disease is likely to progress to acute visceral leishmaniasis may be distinguished from infected patients whose disease is not likely to progress. Such progression may occur within a year (and typically within 5–12 months) for subclinical disease, or within many years in the case of asymptomatic patients. This determination may be made using any of several approaches. In one embodiment, the assay is performed using a polypeptide that comprises at least one repeat unit of the K39 antigen, without the use of an LcP0 epitope. Preferably, the polypeptide comprises the K39 repeat unit antigen described above. While the K39 repeat unit antigen generates a positive result (relative to the predetermined cut-off value) when reacted with sera from more than 97% of patients with acute visceral leishmaniasis, only a relatively small percentage (around one third) of patients with asymptomatic leishmaniasis react with this antigen. Those sera that do react are likely to indicate infections that are in the process of progression, or are likely to progress, to acute visceral leishmaniasis (or infections that are in remission or responding to treatment, which may be distinguished based on patient history).

In another embodiment, the assay is separately performed with LcP0, or an epitope thereof, and with a polypeptide that comprises at least one repeat unit of the K39 antigen. In this embodiment, the optical density (OD) obtained in the assay using the LcP0 epitope is compared to the value obtained using the K39 polypeptide. A relatively high OD in the assay using the LcP0 epitope, along with a relatively low OD in the assay using the K39 polypeptide indicates an asymptomatic or subclinical infection that is not likely to progress to acute visceral leishmaniasis. On the other hand, a relatively high OD in the assay using the K39 polypeptide, along with a relatively low OD in the assay using the LcP0 epitope indicates an asymptomatic or subclinical infection that is likely to progress to acute visceral leishmaniasis (or in remission or responding to treatment). Those asymptomatic or subclinical patients for whom both values are relatively high are likely to be in the process of developing acute visceral leishmaniasis (or in the process of recovering from infection). In each case, the direction of the disease (i.e., progression or remission) may be determined using the patient's history.

In another embodiment, asymptomatic or subclinical patients that are likely to develop acute visceral leishmaniasis may be identified using separate LcP0 and K39 assays (as described above) that are performed over a period of time. For example, the assays may be performed every 1–6 months for a period of months or years. Asymptomatic or subclinical patients that are likely to remain asymptomatic or subclinical will generally have sera that shows a high reactivity with LcP0 and a low reactivity with the K39 polypeptide, as discussed above, at each time point. However, patients that are progressing toward acute visceral leishmaniasis will show an increase in the reactivity with the K39 polypeptide and a decrease in the reactivity with LcP0 over the time period of the assays. By monitoring an individual patient in this manner, the development of acute visceral leishmaniasis may be identified before other symptoms become apparent. This early identification allows selective treatment of only those asymptomatic patients that are predisposed to develop a more serious form of the disease.

In another aspect of this invention, immobilized LcP0 polypeptides may be used to purify antibodies that bind to LcP0. Such antibodies may be prepared by any of a variety of techniques known to those of ordinary skill in the art. See, e.g., Harlow and Land, *Antibodies. A Laboratory Manual*, Cold Spring Harbor Laboratory, 1988. In one such technique, an immunogen comprising a LcP0 polypeptide is initially injected into any of a wide variety of mammals (e.g., mice, rats, rabbits, sheep and goats). In this step, the polypeptide may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In this process, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. One or more LcP0 polypeptides may be used in the purification process in, for example, an affinity chromatography step.

Monospecific antibodies that bind to an LcP0 polypeptide may be used, for example, to detect Leishmania infection in a biological sample using one of a variety of immunoassays, which may be direct or competitive. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen, and the remainder of the sample and antibody is removed. The level of antibody bound to the solid support is inversely related to the level of antigen in the sample. Thus, a lower level of antibody bound to the solid support indicates the presence of Leishmania in the sample. Other formats for using monospecific antibodies to detect Leishmania in a sample will be apparent to those of ordinary skill in the art, and the above formats are provided solely for exemplary purposes.

In another aspect of this invention, vaccines and pharmaceutical compositions are provided for the prevention of Leishmania infection, and complications thereof, in a mammal, preferably a human or dog. Pharmaceutical compositions generally comprise one or more polypeptides, containing one or more epitopes of Leishmania proteins, and a physiologically acceptable carrier. The vaccines comprise one or more of the above polypeptides and an adjuvant, for enhancement of the immune response.

Routes and frequency of administration and polypeptide doses will vary from individual to individual and may parallel those currently being used in immunization against other protozoan infections. In general, the pharmaceutical compositions and vaccines may be administered by injection (e.g., intramuscular, intravenous or subcutaneous), intranasally (e.g., by aspiration) or orally. Between 1 and 4 doses may be administered for a 2–6 week period. Preferably, two doses are administered, with the second dose 2–4 weeks later than the first. A suitable dose is an amount of polypeptide that is effective to raise antibodies in a treated mammal that are sufficient to protect the mammal from Leishmania infection for a period of time. In general, the amount of polypeptide present in a dose ranges from about 1 pg to about 100 mg per kg of host, typically from about 10 pg to about 1 mg, and preferably from about 100 pg to about 1 µg. Suitable dose sizes will vary with the size of the animal, but will typically range from about 0.01 mL to about 5 mL for 10–60 kg animal.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

The following Examples are offered by way of illustration and not by way of limitation.

EXAMPLES

Example 1

Preparation of LcP0

This Example illustrates the isolation of a genomic DNA sequence encoding LcP0 and the preparation of LcP0.

A genomic expression library was constructed with sheared DNA of *L. chagasi* (MHOM/BR/82/BA-2,C1) in bacteriophage λZAPII (Stratagene, La Jolla, Calif.). The library was screened and pBSK(−) phagemid sequences were excised according to the manufacturer's protocols. For this screen, serum samples from 5 *T. cruzi*-infected individuals were pooled and anti-*E. coli* reactivity was removed by adsorption. One clone, containing an approximately 3 kb insert, was isolated (pLcP0). Expression of pLcP0 produced a recombinant fusion protein of approximately 42 kD, of which about 4 kD represented a plasmid fusion sequence.

The DNA sequence (shown in FIGS. 1(*a*) and (*b*)) contained a single open reading frame (nucleotides 1-966) encoding 322 amino acids with a predicted molecular weight of 34,600. Rabbit anti-serum against purified recombinant LcP0 was used to probe immunoblots of *L. chagasi* promastigote lysate. The anti-serum reacted specifically to a 37 kD antigen present in the promastigotes. These results suggest that the recombinant DNA sequence contained the entire coding region of LcP0.

To further verify that the LcP0 genomic clone contained the full-length protein sequence, a cDNA library was screened with the LcP0 clone. Briefly, poly(A)$^+$ RNA was purified from total *L. chagasi* (MHOM/BR/84/Jonas) promastigote RNA, using standard protocols. A cDNA expression library was constructed with the poly(A)$^+$ RNA, using the ZAP-cDNA unidirectional cloning kit (Stratagene, La Jolla, Calif.). This library was screened as described above for the genomic DNA library, and a 1.2 kb cDNA clone was isolated. Partial sequence analysis of the 5' and 3' portions revealed that it encoded a full-length LcP0 insert. The sequence contained the last 8 nucleotides of the trans-spliced leader sequence found on the 5' end of all trypanosome nuclearly-encoded transcripts, followed by a short (29 nucleotide) 5' untranslated leader sequence. Partial sequencing of the 3' portion of the cDNA revealed an open reading frame and a stop codon (TAA) followed by a 203 nucleotide 3'-untranslated portion terminating in a stretch of poly(A) residues. The 5' and 3' ends of the cDNA were present in the genomic clone. Accordingly, the genomic LcP0 clone encodes the complete LcP0 protein.

Full-length LcP0 was produced and purified from *E. coli* transformed with an expression vector containing the genomic clone pLcP0. Purification to homogeneity was accomplished by preparative SDS-PAGE, followed by excision and electroelution of the recombinant antigen. The SDS-PAGE was performed by loading expressed protein onto a 12% polyacrylamide gel in sample buffer (50 mM Tris-HCl, 1% SDS, 10% glycerol, 2% 2-mercaptoethanol, 0.01% bromphenol blue) and running according to standard procedure. A section of the gel was transferred to nitrocellulose for immunoblotting with patient serum for band identification. Bands of interest were excised and gel slices were diced into 2–3 mm cubes and soaked overnight at 4° C. in 2% SDS, 0.4M NH$_4$HCO$_3$ and 0.1% dithiothreitol. The gel pieces and soaking buffer were then placed into an electro-eluter (Bio-Rad Laboratories, Richmond, Calif.). Elution occurred for 6–7 hours at 10 mA per tube in 0.5M NH$_4$HCO$_3$, 0.1% SDS. The eluted fractions were dialyzed against 0.01M NH$_4$HCO$_3$, 0.02% SDS for 24 hours, followed by dialysis against a minimum of 100 volumes of PBS, pH 7.4 for 3–5 days with two buffer changes per 24 hours. All dialysis was done at 4° C. Eluted samples were assayed for protein content using the Pierce assay (Pierce Chemical Co., Rockford, Ill.) and checked for purity on SDS-PAGE minigels with silver staining (Bio-Rad Laboratories, Richmond, Calif.).

Example 2

Detection of Asymptomatic Leishmania using LcP0

This Example illustrates the detection of Leishmania infection using LcP0, prepared as described in Example 1, in an ELISA format.

The ELISA assays were performed as follows. Plastic 96-well plates (Probind, Falcon Plastics, Cockeysville, Md.) were coated with 250 ng of LcP0, diluted to 50 µl with 0.05M carbonate buffer (pH 9.6), and incubated overnight. Sensitized wells were washed with 0.01M phosphate buffered saline (pH 7.2) containing 0.3% Tween 20™ (PBS/T). Positive control, negative control, and unknown serum samples were diluted 1:50 in PBS/T, and 50 µl was added to each well. After 30 minutes of incubation at room temperature, wells were washed six times with PBS/T. Fifty µl of protein-A peroxidase (Zymed Laboratories, San Francisco, Calif.), diluted in PBS/T was added and the plates were incubated as described above. Wells were washed eight times with PBS/T and 100 µl of 2,2'-azino-di-3-ethylbenzethiazoline sulfonic acid (ABTS) substrate solution (50 µl of 50 X ABTS, 50 µl of 1.5% $H_2O_2$, 2.5 ml of 0.1M citrate buffer (pH 4.1), Zymed Laboratories, San Francisco, Calif.) was added. After 15 minutes at room temperature, the enzymatic reaction was stopped by adding 100 µl of 10% sodium dodecylsulfate. $A_{405}$ values were determined with an ELISA reader (Titertek Multiskan, Flow Laboratories, McLean, Va.). The cut-off value was determined for each test by calculating the mean of negative sera plus three standard deviations.

Individuals in Brazil with asymptomatic leishmaniasis (AL) or acute visceral leishmaniasis (AVL) were identified based on serology (e.g., IFAT or IHA immunofluorescence or hemaglutination), clinical symptoms (e.g., malaise, diarrhea, splenomegaly and hepatomegaly) and whole lysate ELISA. Of 21 serum samples from patients with AL, all (i.e., 100%) tested positive using the above assay. However, of 31 serum samples from patients with AVL, only 9 (i.e., 29%) were positive. In addition, 44 normal serum samples (from unexposed individuals in Seattle, Wash.) were assayed. All 44 (i.e., 100%) of the normal samples were negative. When the assay was performed using crude lysate, all 44 normal samples were negative, all 21 AL samples were positive, and 28 out of 31 AVL samples were positive.

Figure 4B:
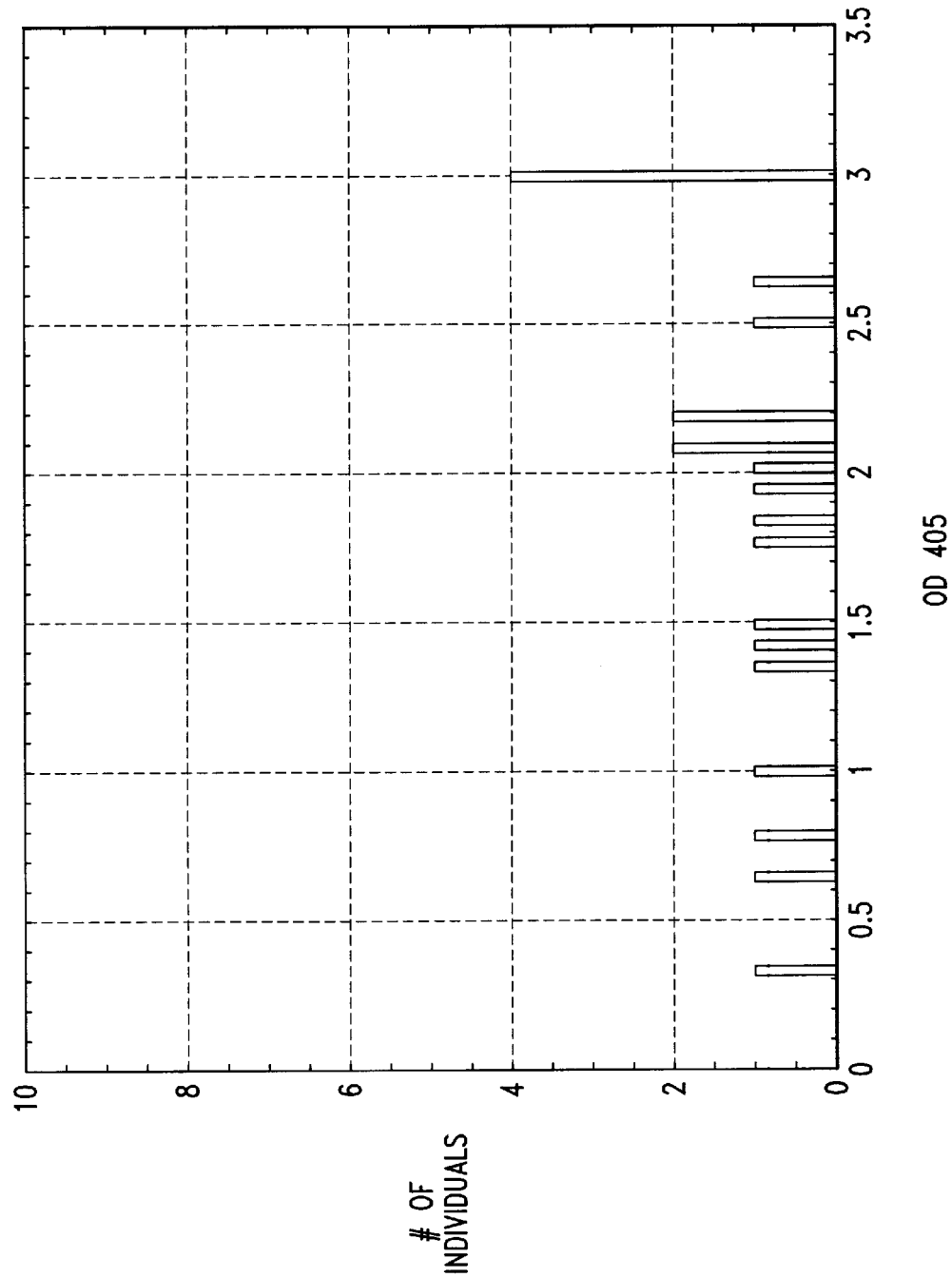
FIG. 4(b) shows the reactivity with asymptomatic patient sera and FIG. 4(c) depicts the reactivity with sera from patients with acute visceral leishmaniasis.
Figure 4C:
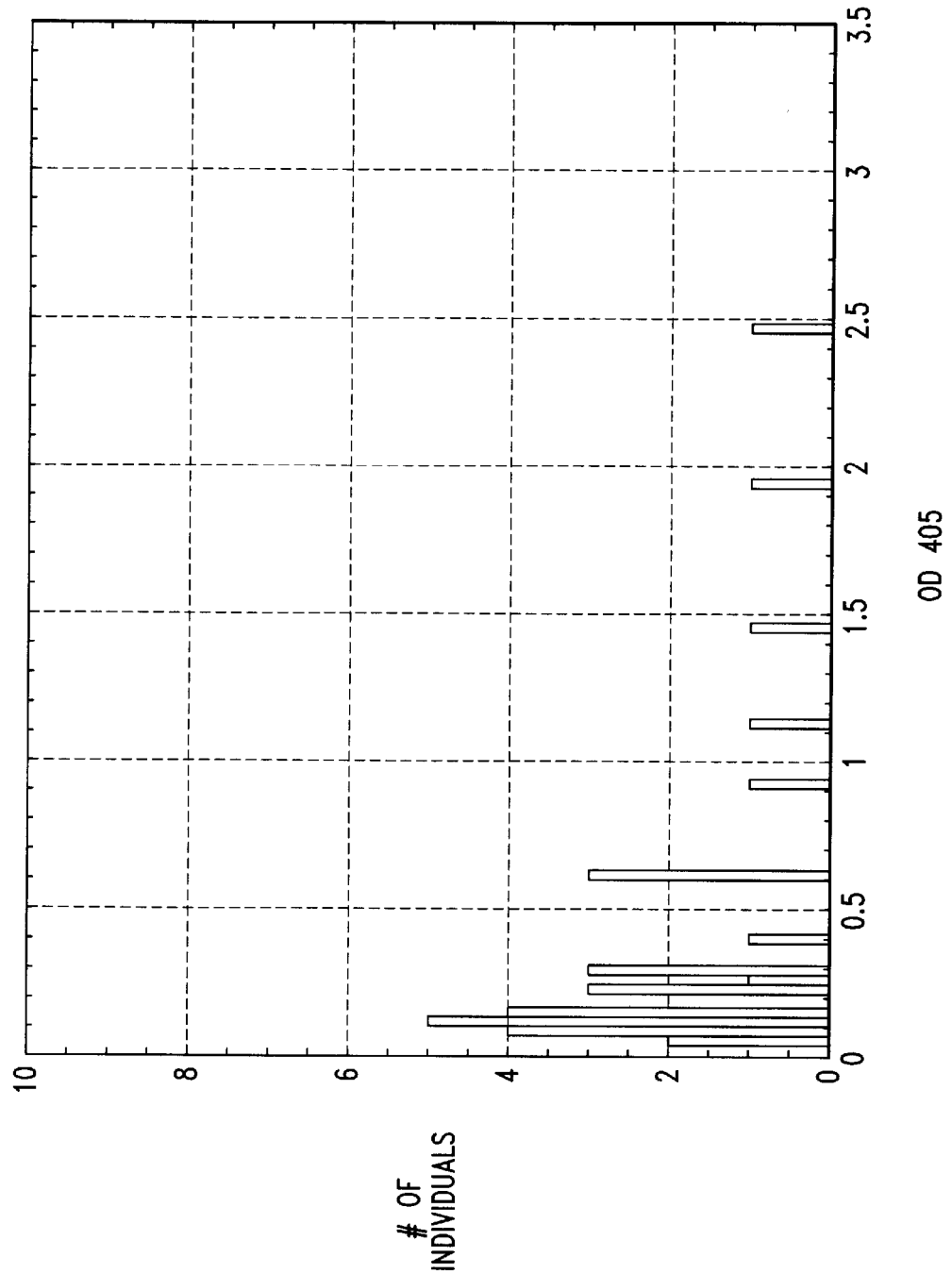

These results are depicted in FIG. 4. FIG. 4(a) shows the distribution of absorbance values at 405 nm for the normal sera assayed with LcP0. In FIG. 4(b), the distribution for sera from individuals with AL is presented and, in FIG. 4(c), the distribution for sera from individuals with AVL is shown.

These results demonstrate that LcP0 may be used to detect asymptomatic leishmaniasis, with a very low incidence of false positive results in normal individuals.

Example 3

Detection of Asymptomatic Leishmania using the C-terminal Epitope of LcP0

This Example illustrates the detection of Leishmania infection using a polypeptide containing the 17 C-terminal amino acids of LcP0 (i.e., residues 306–322) in an ELISA format.

The polypeptide was synthesized on an ABI 430A peptide synthesizer using FMOC chemistry with HPTU (O-Benzotriazole-N,N,N',N'-tetramethyluronium hexafluorophosphate) activation. Cleavage of the polypeptide from the solid support was carried out using the following cleavage mixture: trifluoroacetic acid:ethanedithiol:thioanisole:water:phenol (40:1:2:2:3). After cleaving for 2 hours, the polypeptide was precipitated in cold methyl-t-butyl-ether. The pellet was then dissolved in water containing 0.1% trifluoroacetic acid (TFA) and lyophilized prior to purification by C18 reverse phase HPLC. A gradient of 0%-60% acetonitrile (containing 0.1% TFA) in water (containing 0.1% TFA) was used to elute the peptides. Following lyophilization of the pure fractions, the polypeptide was characterized using electrospray mass spectrometry and by amino acid analysis. The synthesized C-terminal polypeptide had the sequence Glu-Glu-ProGlu-Glu-Ser-Asp-Glu-Asp-Asp-Phe-Gly-Met-Gly-Gly-Leu-Phe (i.e., residues 306–322 of the amino acid sequence of FIGS. 2(a), (b) and (c) and SEQ ID NO:2).

The ELISA assays were performed as described in Example 2, using either 250 ng of LcP0 or 1 µg of the above C-terminal polypeptide. AL, AVL and normal serum samples were assayed. Of 20 serum samples from patients with AL, all tested positive in the assay using full length LcP0, and 19 (i.e., 95%) tested positive with the C-terminal polypeptide. Of 28 serum samples from patients with AVL, 20 (i.e., 28%) were positive. In addition, all 45 (i.e., 100%) of the normal samples were negative.

Figure 5B:
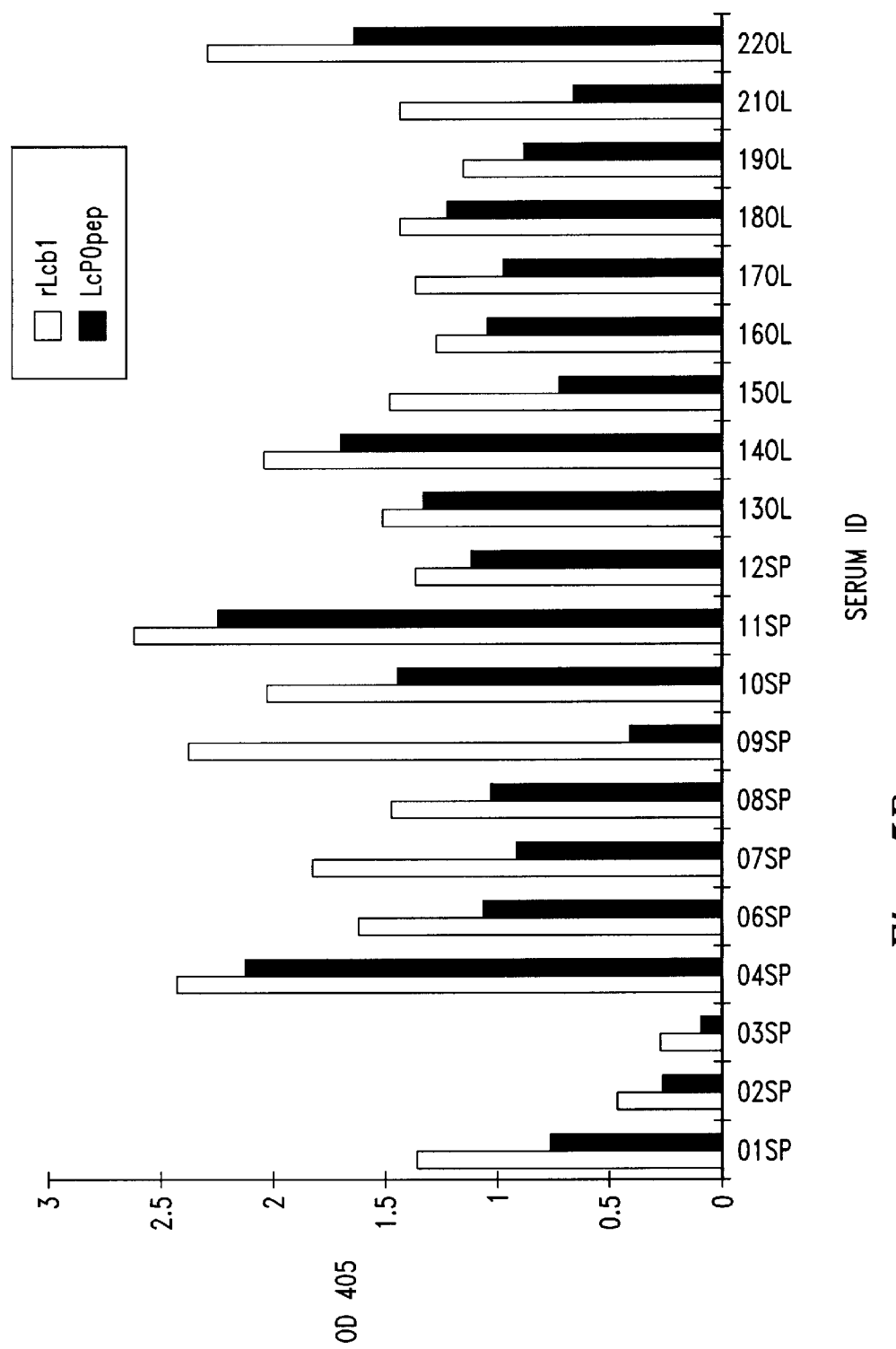
FIG. 5(b) shows the reactivity with asymptomatic patient sera and FIG. 5(c) depicts the reactivity with sera from patients with acute visceral leishmaniasis.
Figure 5C:
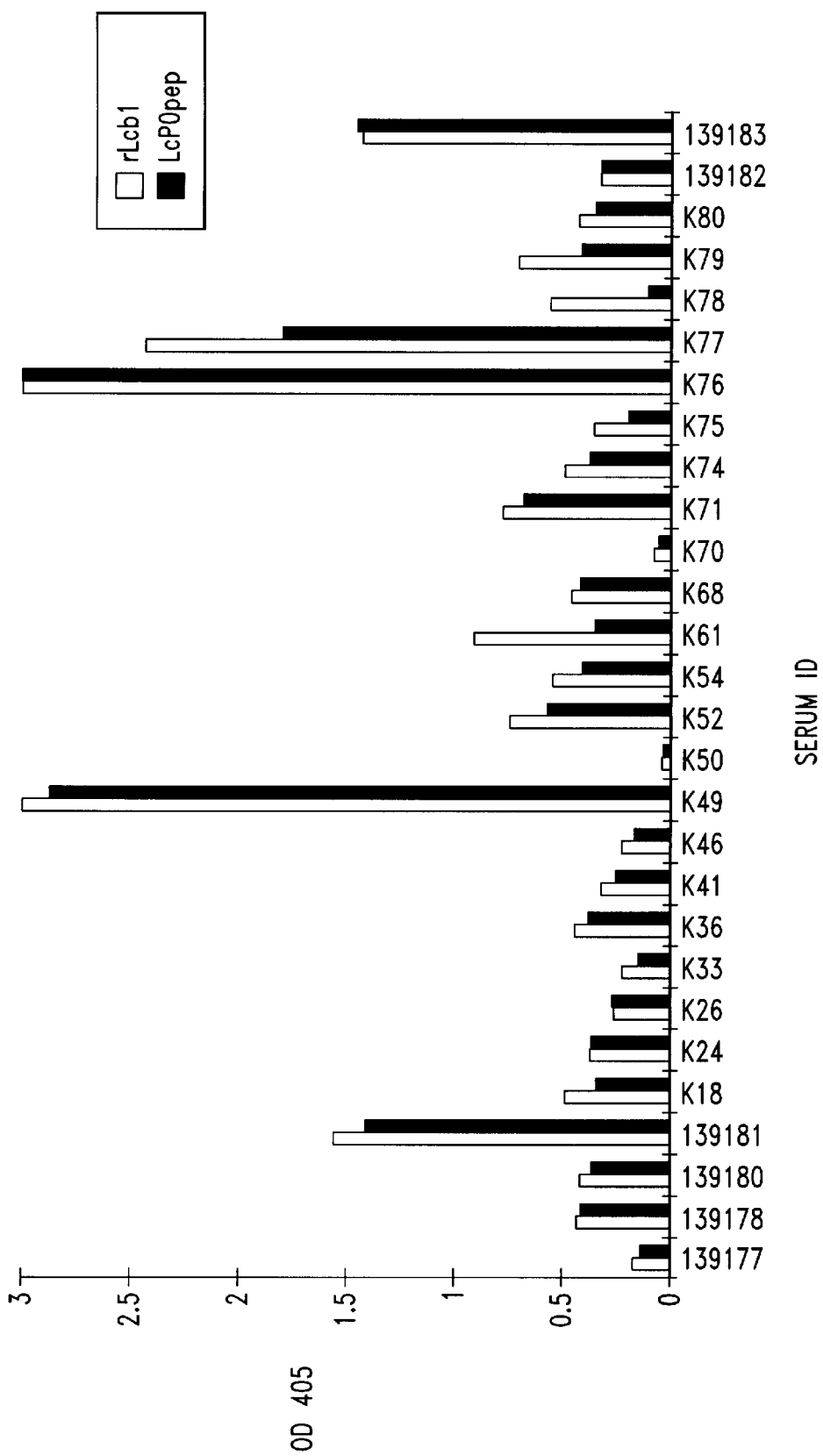

These results are depicted in FIG. 5. FIG. 5(a) shows the distribution of absorbance values at 405 nm for the normal sera assayed with LcP0 and the C-terminal polypeptide. In FIG. 5(b), the distribution for sera from individuals with AL is presented and, in FIG. 5(c), the distribution for sera from individuals with AVL is shown.

These results demonstrate that a polypeptide containing the 17 C-terminal amino acids of LcP0 contains a major epitope and may be used to detect asymptomatic leishmaniasis, with a very low incidence of false positive results in normal individuals.

Example 4

Detection of Leishmania Infection in Serum with K39

This Example demonstrates the detection of Leishmania infection using a recombinant K39 polypeptide.

In one experiment, the assays were performed in an ELISA format, as described in Example 2, except that the wells were coated with 100 ng of recombinant K39 polypeptide having the amino acid sequence shown in FIGS. 2(a), (b) and (c).

In this experiment, the AL, AVL and normal serum samples described in Example 2 were assayed. Of 21 serum samples from patients with AL, 17 (i.e., 33%) tested positive in the assay. However, of 31 serum samples from patients with AVL, 30 (i.e., 97%) were positive. In addition, all 44 (i.e., 100%) of the normal samples were negative.

Figure 6A:
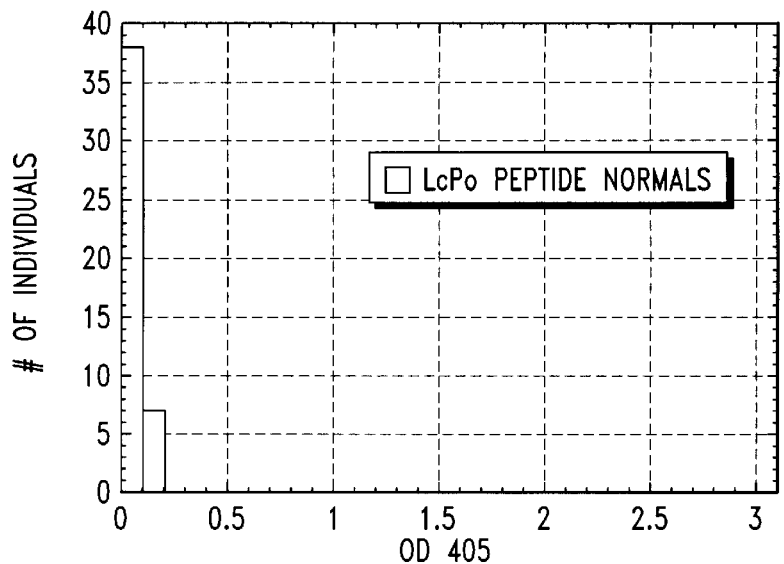
FIG. 6(a) shows the reactivity with sera from normal individuals.
Figure 6B:
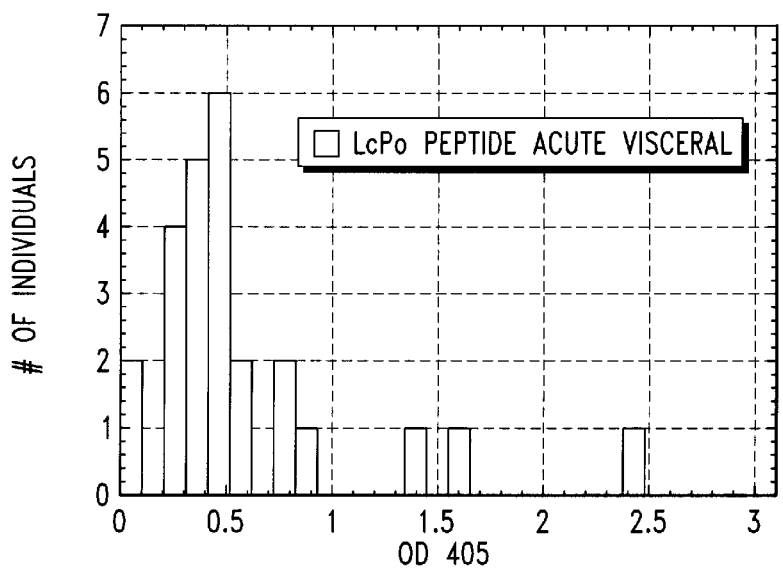
FIG. 6(b) shows the reactivity with sera from patients with acute visceral leishmaniasis and FIG. 6(c) depicts the reactivity with asymptomatic patient sera.
Figure 6C:
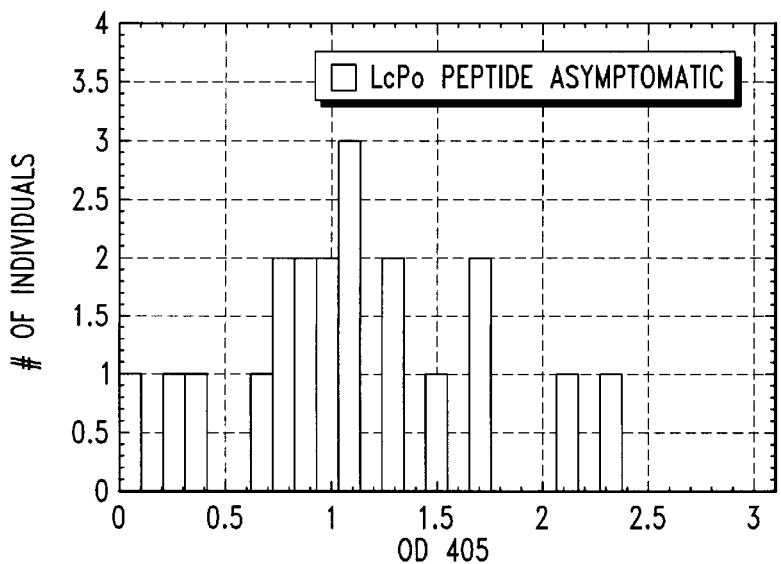

These results are depicted in FIG. 6. FIG. 6(a) shows the distribution of absorbance values at 405 nm for the normal sera assayed with K39. In FIG. 6(b), the distribution for sera from individuals with AVL is presented and, in FIG. 6(c), the distribution for sera from individuals with AL is shown.

These results demonstrate that K39 detects acute visceral leishmaniasis, with a very low incidence of false positive results in normal individuals, but that K39 is not sensitive for detecting asymptomatic leishmaniasis. In addition, FIGS. 4–6, and the results described in Example 2 and this Example, indicate that nearly all patients with AVL or AL (i.e., 60 out of 61) tested positive with at least one of LcP0 and K39. This indicates that the two antigens, used in combination, would detect both types of leishmaniasis.

To further illustrate this point, Table 1, below, shows the absorbance values for the 21 AL samples and the 31 AVL samples tested with LcP0 and K39.

TABLE 1

Reactivity of Serum Samples with LcP0 and K39 Antigens

| | Absorbance (405 nm) | |
|---|---|---|
| Serum | K39 | LcP0 |
| AL | | |
| 01SP | 0.07 | 1.47 |
| 02SP | 0.04 | 0.64 |
| 04SP | 0.1 | >3.0 |
| 05SP | 0.08 | 2.07 |
| 06SP | 0.06 | 1.95 |
| 07SP | 0.33 | 2.18 |
| 08SP | 0.08 | 2.02 |
| 09SP | 0.10 | >3.0 |
| 10SP | 0.62 | 2.49 |
| 11SP | 0.08 | >3.0 |
| 12SP | 0.88 | 1.77 |
| 13OL | 0.10 | 2.07 |
| 14OL | 0.07 | 2.65 |
| 15OL | 0.03 | 2.19 |
| 16OL | 0.12 | 1.35 |
| 17OL | >3.0 | 0.78 |
| 19OL | 0.11 | 1.41 |
| 21OL | 0.29 | 1.84 |
| 22OL | 2.42 | >3.0 |
| 25aPK | 0.11 | 0.35 |
| 27PK | 0.92 | 0.98 |
| AVL | | |
| K8 | 2.31 | 0.12 |
| K22 | 1.47 | 0.08 |
| K36 | 2.52 | 0.16 |
| K39 | 2.60 | 0.39 |
| K49 | 2.50 | 1.94 |
| K52 | >3.0 | 0.25 |
| K2 | >3.0 | 2.48 |
| K7 | >3.0 | 0.17 |
| K11 | 1.58 | 0.07 |
| K18 | >3.0 | 0.28 |
| K24 | >3.0 | 0.17 |
| K26 | 2.60 | 0.08 |
| K33 | 2.22 | 0.11 |
| K41 | >3.0 | 0.24 |
| K46 | >3.0 | 0.23 |
| K50 | 2.31 | 0.01 |
| K54 | 2.70 | 0.22 |
| K61 | >3.0 | 1.14 |
| K68 | >3.0 | 0.12 |
| K70 | >3.0 | 0.08 |
| K71 | >3.0 | 0.30 |
| K74 | >3.0 | 0.17 |
| K2 | >3.0 | 0.61 |
| K50 | 1.27 | 0.02 |
| K68 | >3.0 | 0.60 |
| 139177 | 0.09 | 0.13 |
| 139178 | 0.38 | 0.13 |
| 139180 | 0.28 | 0.31 |
| 139181 | >3.0 | 0.93 |
| 139182 | 0.66 | 0.62 |
| 139183 | 1.97 | 1.44 |

As shown in the above table, most samples with very low absorbance values when assayed with one antigen had high absorbances when assayed with the other antigen. Accordingly, LcP0 and K39 are complementary and, together, form a sensitive assay for monitoring disease progression from asymptomatic/subclinical disease to acute visceral disease, or vice versa.

Example 5
Detection of Leishmania Infection in Serum with LcP0 in Combination with K39

This Example demonstrates the detection of Leishmania infection using LcP0 in combinantion K39 polypeptide.

Assays were performed as described in Example 2 except that, in addition to the LcP0, wells were coated with 100 ng of recombinant K39. In a parallel experiment, the assays were performed using Leishmania lysate as the antigen. The same AL, AVL and normal serum samples described in Example 2 were assayed. Of the 21 serum samples from patients with AL, 21 (i.e., 100%) tested positive in the assay. Of 31 samples from patients with AVL, 30 (i.e., 97%) were positive. All (i.e., 100%) of the normal samples were negative.

The absorbance values for representative assays using LcP0/K39 or Leishmania lysate are shown in Table 2 below.

TABLE 2

Reactivity of Serum Samples With Leishmania Lysate and K39/LcP0 Antigens

| SAMPLE ID | Lc LYSATE | K39 + LcP0 | STATUS |
|---|---|---|---|
| 01-SP | 1.545 | 1.148 | ASYMPTOMATIC |
| 02-SP | 1.174 | 0.34 | ASYMPTOMATIC |
| 03-SP | 1.263 | 0.168 | ASYMPTOMATIC |
| 04-SP | 2.533 | 2.521 | ASYMPTOMATIC |
| 06-SP | 1.478 | 1.556 | ASYMPTOMATIC |
| 07-SP | 1.365 | 1.701 | ASYMPTOMATIC |
| 08-SP | 1.192 | 1.369 | ASYMPTOMATIC |
| 22OL | 1.669 | 3 | ASYMPTOMATIC |
| 10SP | 1.651 | 1.951 | ASYMPTOMATIC |
| 14OL | 1.192 | 2.061 | ASYMPTOMATIC |
| 15OL | 0.863 | 1.461 | ASYMPTOMATIC |
| 16OL | 2.104 | 1.067 | ASYMPTOMATIC |
| 17OL | 3 | 3 | ASYMPTOMATIC |
| 18OL | 2.032 | 1.264 | ASYMPTOMATIC |
| 19OL | 1.586 | 0.908 | ASYMPTOMATIC |
| 21OL | 1.52 | 1.572 | ASYMPTOMATIC |
| 139189 | 0.348 | 0.431 | AVL |
| 139197 | 0.481 | 2.455 | AVL |
| 139199 | 1.235 | 2.601 | AVL |
| 139200 | 2.022 | 0.792 | AVL |
| 139202 | 1.182 | 0.263 | AVL |
| 139204 | 1.375 | 0.964 | AVL |
| 139205 | 3 | 3 | AVL |
| 139206 | 2.209 | 3 | AVL |
| K18 | 0.95 | 3 | AVL |
| K26 | 1.298 | 3 | AVL |
| K41 | 3 | 3 | AVL |
| K52 | 3 | 3 | AVL |
| K54 | 3 | 3 | AVL |
| K74 | 2.509 | 3 | AVL |
| K71 | 3 | 3 | AVL |
| K75 | 2.118 | 3 | AVL |
| 4/15/93-2 | 0.003 | 0.004 | NORMAL |
| 4/15/93-3 | 0.001 | 0.007 | NORMAL |
| 4/15/93-4 | 0.001 | 0.004 | NORMAL |
| 6/15/93-3 | 0 | 0.002 | NORMAL |
| 6/15/93-2 | 0.001 | 0.004 | NORMAL |
| 2/9/94-4 | 0.003 | 0.003 | NORMAL |
| 2/9/94-3 | 0.003 | 0.001 | NORMAL |
| 2/9/94-2 | 0.005 | 0.006 | NORMAL |
| 9/9/93-2 | 0.17 | 0.046 | NORMAL |
| 7/22/94-4 | 0.034 | 0.049 | NORMAL |
| 7/22/94-3 | 0.055 | 0.055 | NORMAL |
| 7/22/94-2 | 0.034 | 0.066 | NORMAL |
| 7/22/94-1 | 0.029 | 0.051 | NORMAL |
| 3/25/94-4 | 0.035 | 0.023 | NORMAL |
| 3/25/94-3 | 0.02 | 0.021 | NORMAL |

Figure 7A:
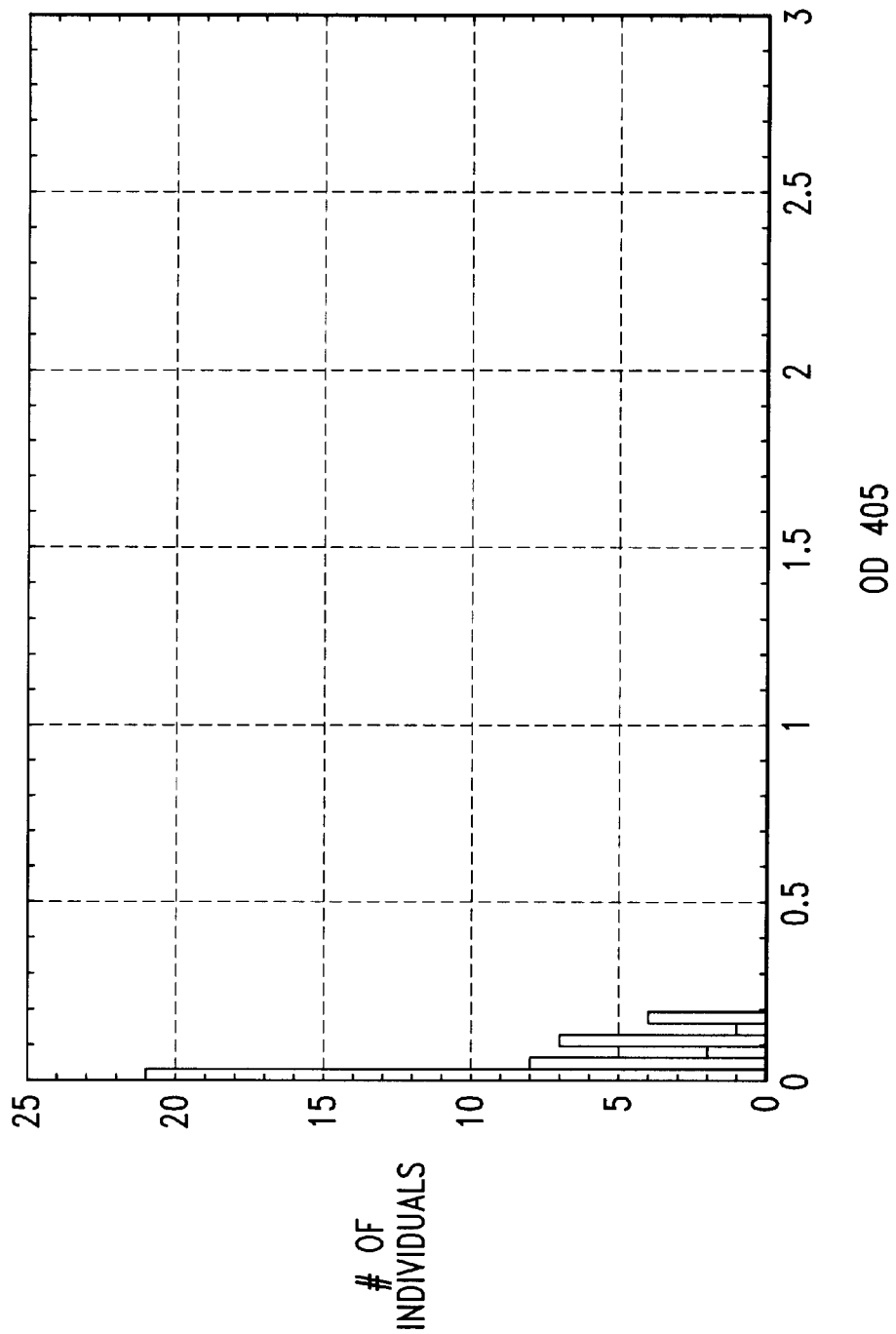
FIG. 7(a) shows the reactivity with sera from normal individuals.
Figure 7B:
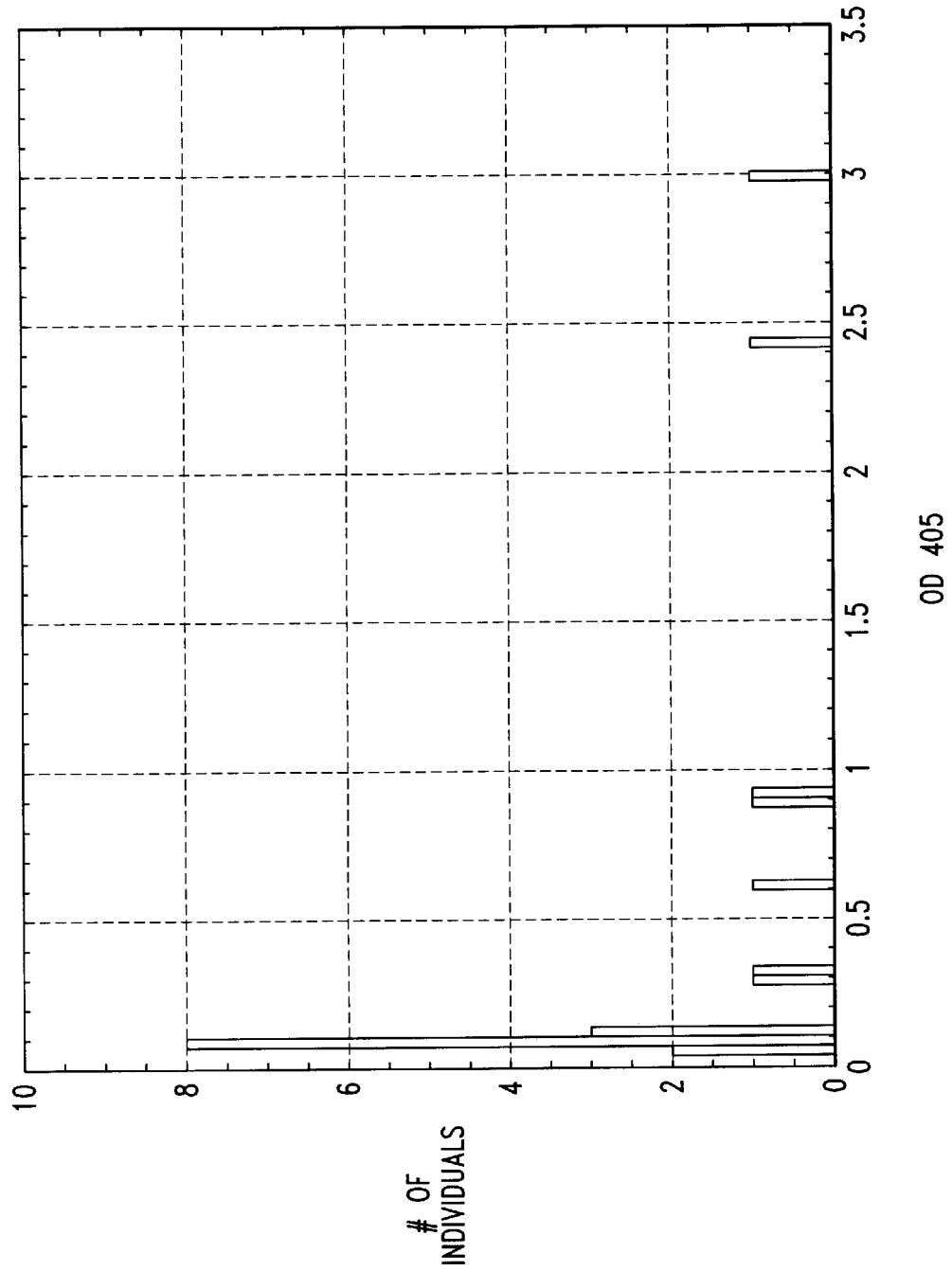
FIG. 7(b) shows the reactivity with asymptomatic patient sera and FIG. 7(c) depicts the reactivity with sera from patients with acute visceral leishmaniasis.
Figure 7C:
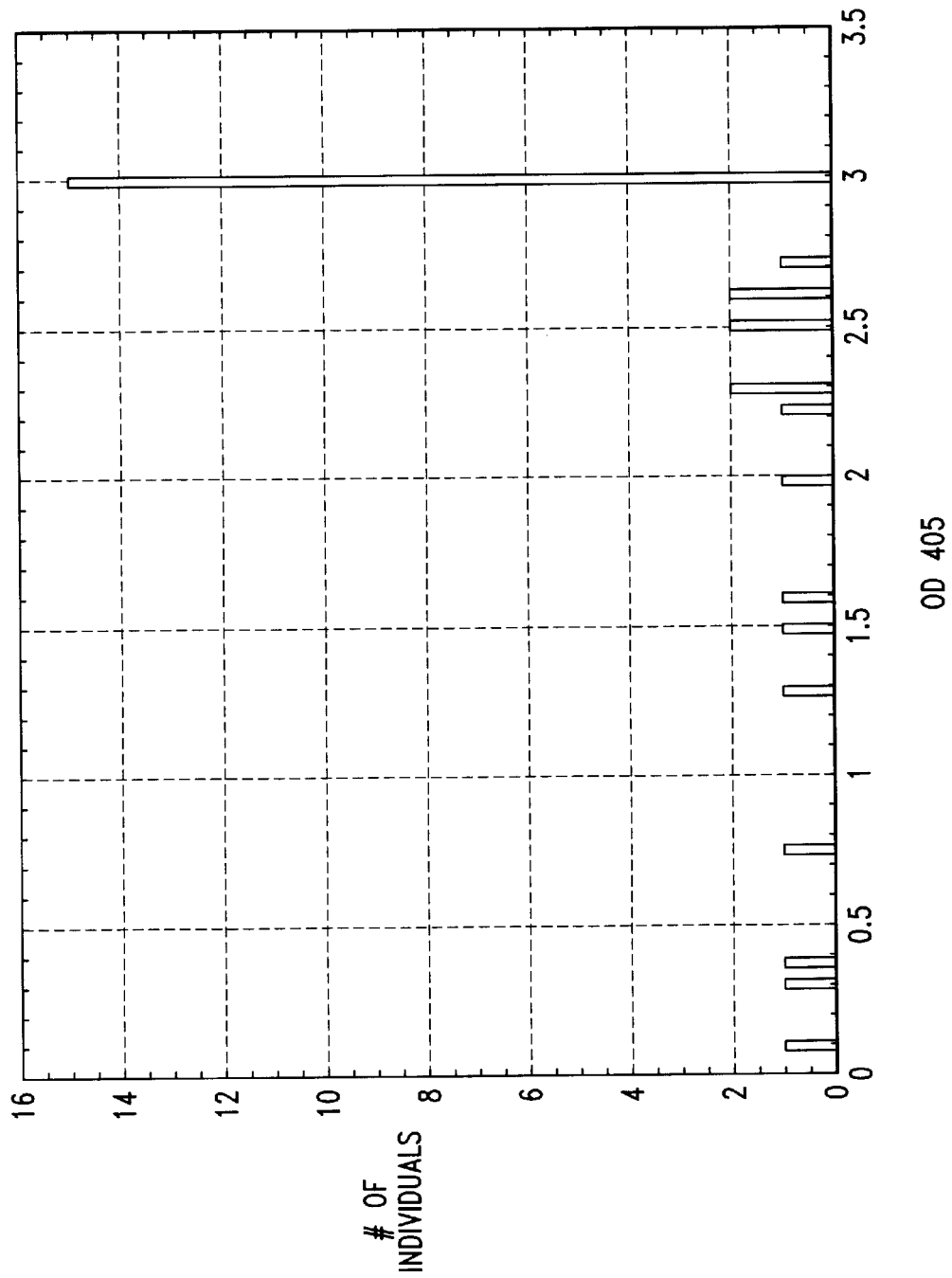

The absorbance values provided above are depicted in FIG. 7, which shows the distribution of absorbance values at 405 nm for assays performed using representative sera from normal AL and AVL patients. The results of this experiment demonstrate that LcP0, combination with K39, detects asymptomatic and acute visceral leishmaniasis, with a very low incidence of false positive results in normal individuals.

Example 6

Non-reactivity of LcP0 and K39 with Sera from Patients with Mucosal or Cutaneous Leishmaniasis This Example shows that LcP0 and K39 are specific for asymptomatic/subclinical and visceral leishmaniasis, respectively. Assays were generally performed as described in Examples 4 and 5, except that the sera assayed was from patients with mucosal or cutaneous leishmaniasis, as diagnosed by clinical symptoms. Fourteen samples from patients with each form of the disease were assayed with LcP0, K39 and a combination of LcP0 and K39, as well as with Leishmania lysate. With each set of 14 samples, a positive control (i.e., a sample obtained from a patient infected with Leishmania) and a blank with no antibodies were assayed, in addition to eight samples from normal individuals.

The absorbance values are shown below in Table 3.

TABLE 3

Non-reactivity of LcP0 and K39 With Sera From Patients With Mucosal and Cutaneous Leishmaniasis

| Serum | Lc lysate | K39 + LcP0 | K39 | LcP0 |
|---|---|---|---|---|
| MUCOSAL | | | | |
| M1 | 0.312 | 0.033 | 0.03 | 0.011 |
| M2 | 0.11 | 0.036 | 0.015 | 0.029 |
| M3 | 0.37 | 0.054 | 0.003 | 0.055 |
| M4 | 0.109 | 0.039 | 0.036 | 0.007 |
| M5 | 0.586 | 0.02 | 0.009 | 0.016 |
| M6 | 0.116 | 0.038 | 0.025 | 0.017 |
| M7 | 0.245 | 0.156 | 0.099 | 0.067 |
| M8 | 0.09 | 0.078 | 0.05 | 0.047 |
| M9 | 0.046 | 0.026 | 0.026 | 0.003 |
| M10 | 0.343 | 0.042 | 0.013 | 0.033 |
| M11 | 0.327 | 0.34 | 0.009 | 0.346 |
| M12 | 0.035 | 0.014 | 0.003 | 0.008 |
| M13 | 0.131 | 0.031 | 0.026 | 0.007 |
| M14 | 0.282 | 0.014 | 0.006 | 0.006 |
| positive control | 0.444 | 0.543 | 0.545 | 0.114 |
| No Ab | 0.001 | 0.002 | −0.002 | −0.001 |
| CUTANEOUS | | | | |
| C1 | 0.06225 | 0.01255 | 0.00725 | 0.0033 |
| C2 | 0.1602 | 0.01225 | 0.00325 | 0.0083 |
| C3 | 0.1402 | 0.03925 | 0.02625 | 0.0143 |
| C4 | 0.1932 | 0.01725 | 0.01325 | 0.0053 |
| C5 | 0.1672 | 0.04825 | 0.01725 | 0.0283 |
| C6 | 0.1672 | 0.02825 | 0.01925 | 0.0213 |

TABLE 3-continued

Non-reactivity of LcP0 and K39 With Sera From Patients With Mucosal and Cutaneous Leishmaniasis

| Serum | Lc lysate | K39 + LcP0 | K39 | LcP0 |
|---|---|---|---|---|
| C7 | 0.09025 | 0.07425 | 0.07225 | 0.0103 |
| C8 | 0.05425 | 0.01725 | 0.00725 | 0.0103 |
| C9 | 0.0803 | 0.05525 | 0.05425 | 0.007 |
| C10 | 0.2702 | 0.04825 | 0.03225 | 0.019 |
| C11 | 0.4882 | 0.3782 | 0.1992 | 0.297 |
| C12 | 0.5632 | 0.5352 | 0.5312 | −0.002 |
| C13 | 0.0263 | 0.01425 | 0.00425 | 0.005 |
| C14 | 0.0293 | 0.01525 | 0.01525 | 0.003 |
| positive control | 0.4132 | 0.5732 | 0.5362 | 0.096 |
| No Ab | 0.0043 | 0.00025 | −0.00275 | −0.002 |
| NORMAL | | | | |
| 6/8/93-1 | 0.018 | 0.01 | 0.005 | 0.005 |
| 6/8/93-2 | 0.03 | 0.01 | 0.005 | 0.006 |
| 6/8/93-3 | 0.016 | 0.02 | 0.012 | 0.003 |
| 8/31/93-3 | 0.018 | 0.14 | 0.002 | 0.01 |
| 8/31/93-4 | 0.003 | 0.005 | −4E−09 | 0.005 |
| 9/10/93-2 | 0.006 | 0.004 | −4E−09 | 0.002 |
| 9/10/93-3 | 0.005 | −3.7E−09 | −0.001 | −4E−09 |
| 4/15/93-2 | 0.014 | 0.043 | 0.037 | 0.009 |
| 1/12/93 | 0.0023 | 0.00725 | 0.0013 | 0.0003 |
| 3/2/94-4 | 0.0013 | 0.00025 | −0.0028 | 0.0003 |
| 3/2/94-3 | −0.002 | −0.00275 | −0.0048 | −0.006 |
| 3/2/94-2 | 0.0003 | 0.00025 | −0.0008 | −0.008 |
| 3/2/94-1 | 0.0043 | 0.00225 | −0.0048 | 0.0033 |
| 4/28/94-3 | −0.002 | −0.00375 | −0.0058 | −0.012 |
| 4/28/94-2 | 0.0083 | 0.00225 | −0.0028 | 0.0003 |
| 4/15/93-2 | 0.0123 | 0.04325 | 0.0333 | 0.0023 |

Of the normal serum samples assayed, no positive results were obtained using either LcP0 or K39, or a combination of the two. Of the 14 mucosal samples, one tested positive with LcP0 and LcP0/K39, and none were positive with K39 alone. When the 14 cutaneous samples were assayed, one tested positive with each of LcP0 and K39, and two were positive with the LcP0/K39 combination. These results demonstrate that assays performed using LcP0 and/or K39 detect only a small percentage of mucosal and cutaneous manifestations of leishmaniasis.

From the foregoing, it will be appreciated that, although specific embodiments of the invention have been described herein for the purpose of illustration, various modifications may be made without deviating from the spirit and scope of the invention.

We claim:

1. A method for detecting asymptomatic or sub-clinical Leishmania infection in a biological sample selected from the group consisting of sera, blood, and saliva, comprising:
    (a) contacting a biological sample with a polypeptide comprising an epitope of LcP0; and
    (b) detecting in the biological sample the presence of antibodies that bind to the polypeptide, thereby detecting asymptomatic or sub-clinical Leishmania infection in the biological sample.

2. The method of claim 1 wherein the epitope of LcP0 comprises amino acids 306–322 of SEQ ID NO:2.

3. The method of claim 1 wherein the polypeptide is bound to a solid support.

4. The method of claim 3 wherein the solid support comprises nitrocellulose, latex or a plastic material.

5. The method of claim 3 wherein the step of detecting comprises:
    (a) removing unbound sample from the solid support;
    (b) adding a detection reagent to the solid support; and (c) determining the level of detection reagent bound to the solid support, relative to a predetermined cutoff value, thereby detecting asymptomatic or sub-clinical Leishmania infection in the biological sample.

6. A method for detecting Leishmania infection in a biological sample selected from the group consisting of sera, blood, and saliva, comprising:

(a) contacting a biological sample with a first amino acid sequence comprising an epitope of LcP0;

(b) contacting the biological sample with a second amino acid sequence comprising an amino acid sequence of SEQ ID NO:5; and (c) detecting in the sample the presence of antibodies that bind to one or both of the amino acid sequences, thereby detecting Leishmania infection in the biological sample.

7. The method of claim 6 wherein the epitope of LcP0 comprises amino acids 306–322 of SEQ ID NO:2.

8. The method of claim 6 wherein the first and second amino acid sequences are bound to a solid support.

9. The method of claim 8 wherein the solid support comprises nitrocellulose, latex or a plastic material.

10. The method of claim 8 wherein the step of detecting comprises:

(a) removing unbound sample from the solid support;

(b) adding a detection reagent to the solid support; and (c) determining the level of detection reagent bound to the solid support, relative to a predetermined cutoff value, therefrom detecting Leishmania in the biological sample.

11. A method of identifying a patient afflicted with asymptomatic or subclinical leishmaniasis that is likely to develop acute visceral leishmaniasis, comprising:

(a) contacting a biological sample obtained from a patient afflicted with asymptomatic or subclinical leishmaniasis with a first polypeptide comprising an epitope of LcP0, the biological sample being selected from the group consisting of sera, blood, and saliva;

(b) independently contacting the biological sample with a second polypeptide comprising the amino acid sequence of SEQ ID NO:5; and (c) detecting in the sample the presence of antibodies that bind to at least one of the first and second polypeptides, thereby identifying a patient afflicted with asymptomatic or subclinical leishmaniasis that is likely to develop acute visceral leishmaniasis.

12. The method of claim 11 wherein the epitope of LcP0 comprises amino acids 306–322 of SEQ ID NO:2.

13. The method of claim 11 wherein the first and second polypeptides are each bound to a separate solid support.

14. The method of claim 13 wherein the solid supports comprise nitrocellulose, latex or a plastic material.

15. The method of claim 13 wherein the step of detecting comprises:

(a) removing unbound sample from each solid support;

(b) adding a detection reagent to each solid support; and (c) comparing the level of detection reagent bound to each solid support, relative to a predetermined cutoff value, therefrom identifying a patient afflicted with asymptomatic or subclinical leishmaniasis that is likely to develop acute visceral leishmaniasis.

16. The method of any of claims 5, 10 or 15 wherein the detection reagent comprises a reporter group conjugated to a binding agent.

17. The method of claim 16 wherein the binding agent is selected from the group consisting of anti-immunoglobulin, Protein G, Protein A and lectins.

18. The method of claim 16 wherein the reporter group is selected from the group consisting of radioisotopes, fluorescent groups, luminescent groups, enzymes, biotin and dye particles.

19. A diagnostic kit for detecting asymptomatic or subclinical leishmaniasis in a biological sample selected from the group consisting of sera, blood, and saliva, comprising:

(a) a polypeptide comprising an epitope of LcP0; and (b) a detection reagent.

20. A diagnostic kit for detecting Leishmania infection in a biological sample selected from the group consisting of sera, blood, and saliva, comprising:

(a) a first amino acid sequence comprising an epitope of LcP0;

(b) a second amino acid sequence comprising the amino acid sequence of SEQ ID NO:5; and (c) a detection reagent.

21. A diagnostic kit for identifying a patient afflicted with asymptomatic or subclinical leishmaniasis that is likely to develop acute visceral leishmaniasis, comprising:

(a) a first polypeptide comprising an epitope of LcP0;

(b) a second polypeptide comprising the amino acid sequence of SEQ ID NO:5; and (c) a detection reagent.

22. The kit of any of claims 19, 20 or 21 wherein the detection reagent comprises a reporter group conjugated to a binding agent.

23. The kit of claim 22 wherein the binding agent is selected from the group consisting of anti-immunoglobulin, Protein G, Protein A and lectins.

24. The kit of claim 22 wherein the reporter group is selected from the group consisting of radioisotopes, fluorescent groups, luminescent groups, enzymes, biotin and dye particles.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1202 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 30..998

(xi) SEQUENCE DESCRIPTION: SEQ ID NO:1:

```
ATAGCCAAGG CTATTGCAAG TCTCACAAG ATG CCG TCT ATC ACC ACT GCC AAG        53
                                  Met Pro Ser Ile Thr Thr Ala Lys
                                   1               5

CGC GAG TAC GAG GAG CGC CTC GTC GAC TGC CTG ACC AAG TAC AGC TGC       101
Arg Glu Tyr Glu Glu Arg Leu Val Asp Cys Leu Thr Lys Tyr Ser Cys
         10              15                  20

GTG CTG TTC GTG GGC ATG GAC AAC GTC CGC TCG CAG CAG GTG CAC GAT       149
Val Leu Phe Val Gly Met Asp Asn Val Arg Ser Gln Gln Val His Asp
 25              30                  35                  40

GTG CGC CGT GGC TGT CGC GGC AAG GCC GAG TTC ATT ATG GGC AAG AAG       197
Val Arg Arg Gly Cys Arg Gly Lys Ala Glu Phe Ile Met Gly Lys Lys
                 45                  50                  55

ACG CTG CAG GCG AAG ATC GTG GAG AAG CGC GCG CAA GCC AAG GAC GCG       245
Thr Leu Gln Ala Lys Ile Val Glu Lys Arg Ala Gln Ala Lys Asp Ala
             60                  65                  70

AGC CCC GAG GCG AAG CCT TTC AAC GAT CAG TGT GAG GAG TAC AAC CTG       293
Ser Pro Glu Ala Lys Pro Phe Asn Asp Gln Cys Glu Glu Tyr Asn Leu
         75                  80                  85

CTG AGC GGC AAC ACC GGC CTC ATC TTC ACT AAC AAC GCT GTC CAG GAG       341
Leu Ser Gly Asn Thr Gly Leu Ile Phe Thr Asn Asn Ala Val Gln Glu
     90                  95                 100

ATC ACC TCT GTG CTT GAC GGC CAC CGC GTG AAG GCC CCG GCG CGT GTC       389
Ile Thr Ser Val Leu Asp Gly His Arg Val Lys Ala Pro Ala Arg Val
105             110                 115                 120

GGA GCG ATT CCG TGC GAC GTG GTT GTG CCT GCT GGC AGC ACC GGC ATG       437
Gly Ala Ile Pro Cys Asp Val Val Val Pro Ala Gly Ser Thr Gly Met
                125                 130                 135

GAG CCG ACC CAG ACG TCC TTC TTC CAG GCG CTG AAC ATT GCG ACG AAG       485
Glu Pro Thr Gln Thr Ser Phe Phe Gln Ala Leu Asn Ile Ala Thr Lys
            140                 145                 150

ATT GCC AAG GGT ATG GTG GAG ATC GTG ACG GAG AAG AAG GTG CTG AGC       533
Ile Ala Lys Gly Met Val Glu Ile Val Thr Glu Lys Lys Val Leu Ser
        155                 160                 165

GTC GGC GAC AAG GTG GAC AAC TCG ACG GCG ACG CTG CTG CAA AAG CTG       581
Val Gly Asp Lys Val Asp Asn Ser Thr Ala Thr Leu Leu Gln Lys Leu
        170                 175                 180

AAC ATC AGC CCG TTC TAC TAC CAG GTG AAT GTG CTG TCC GTG TGG GAC       629
Asn Ile Ser Pro Phe Tyr Tyr Gln Val Asn Val Leu Ser Val Trp Asp
185                 190                 195                 200

CGC GGT GTG CTG TTC ACC CGC GAG GAC CTC ATG ATG ACG GAG GAC ATG       677
Arg Gly Val Leu Phe Thr Arg Glu Asp Leu Met Met Thr Glu Asp Met
                205                 210                 215

GTG GAG AAG ATG CTG ATG GAA GGC CTG AGC AAC GTT GCG GCG ATG GCG       725
Val Glu Lys Met Leu Met Glu Gly Leu Ser Asn Val Ala Ala Met Ala
                220                 225                 230

CTG GGT GCT GGC ATC CCG ACG TCT TCG ACG ATT GGC CCG ATG CTG GTG       773
Leu Gly Ala Gly Ile Pro Thr Ser Ser Thr Ile Gly Pro Met Leu Val
        235                 240                 245

GAC GCC TTC AAG AAC CTG CTG GCT GTC TCC GTG GCG ACC TCG TAC GAG       821
Asp Ala Phe Lys Asn Leu Leu Ala Val Ser Val Ala Thr Ser Tyr Glu
        250                 255                 260

TTC GAG GAG CAC AAC GGC AAG GAG CTG CGC GAG GCC GCG ATC AAC GGC       869
Phe Glu Glu His Asn Gly Lys Glu Leu Arg Glu Ala Ala Ile Asn Gly
265                 270                 275                 280

CTG CTG GCC GGC TCT GGC TCG GCT GCT GCG GAG CCC GCC GCT GCC GCG       917
Leu Leu Ala Gly Ser Gly Ser Ala Ala Ala Glu Pro Ala Ala Ala Ala
                285                 290                 295

CCG GCC GCC CCT AGC GCT GCT GCC AAG GAG GAG CCG GAG GAG AGC GAC       965
```

```
Pro Ala Ala Pro Ser Ala Ala Ala Lys Glu Glu Pro Glu Glu Ser Asp
            300                 305                 310

GAG GAC GAC TTC GGC ATG GGC GGT CTC TTC TAA GCGACTCGCT ATCCGCCACC     1018
Glu Asp Asp Phe Gly Met Gly Gly Leu Phe  *
            315                 320

CAGCACCGTC GAGTGTTCGT GCGTTCGCAT GGTGGACAGT GGCGAGCGTG TGATGCCCTT     1078

GGATCATCAG GAAGCAACTC TCTCCCTTTC TCTGGGTGTT CTTCGTTTCT TCTTTCATTT     1138

GTTTTTGATC GCCGTGGCGC TGCGGCGATC GCTCAGTTCT TATTTTCGAT CAACCAACAA     1198

CGAA                                                                   1202

(2) INFORMATION FOR SEQ ID NO:2:

(i) SEQUENCE CHARACTERISTICS:
         (A) LENGTH: 322 amino acids
         (B) TYPE: amino acid
         (D) TOPOLOGY: linear (ii) MOLECULE TYPE: protein (xi) SEQUENCE DESCRIPTION: SEQ ID NO:2:

Met Pro Ser Ile Thr Thr Ala Lys Arg Glu Tyr Glu Arg Leu Val
 1               5                  10                  15

Asp Cys Leu Thr Lys Tyr Ser Cys Val Leu Phe Val Gly Met Asp Asn
                20                  25                  30

Val Arg Ser Gln Gln Val His Asp Val Arg Arg Gly Cys Arg Gly Lys
            35                  40                  45

Ala Glu Phe Ile Met Gly Lys Lys Thr Leu Gln Ala Lys Ile Val Glu
    50                  55                  60

Lys Arg Ala Gln Ala Lys Asp Ala Ser Pro Glu Ala Lys Pro Phe Asn
65                  70                  75                  80

Asp Gln Cys Glu Glu Tyr Asn Leu Leu Ser Gly Asn Thr Gly Leu Ile
                85                  90                  95

Phe Thr Asn Asn Ala Val Gln Glu Ile Thr Ser Val Leu Asp Gly His
                100                 105                 110

Arg Val Lys Ala Pro Ala Arg Val Gly Ala Ile Pro Cys Asp Val Val
            115                 120                 125

Val Pro Ala Gly Ser Thr Gly Met Glu Pro Thr Gln Thr Ser Phe Phe
130                 135                 140

Gln Ala Leu Asn Ile Ala Thr Lys Ile Ala Lys Gly Met Val Glu Ile
145                 150                 155                 160

Val Thr Glu Lys Lys Val Leu Ser Val Gly Asp Lys Val Asp Asn Ser
                165                 170                 175

Thr Ala Thr Leu Leu Gln Lys Leu Asn Ile Ser Pro Phe Tyr Tyr Gln
                180                 185                 190

Val Asn Val Leu Ser Val Trp Asp Arg Gly Val Leu Phe Thr Arg Glu
            195                 200                 205

Asp Leu Met Met Thr Glu Asp Met Val Glu Lys Met Leu Met Glu Gly
    210                 215                 220

Leu Ser Asn Val Ala Ala Met Ala Leu Gly Ala Gly Ile Pro Thr Ser
225                 230                 235                 240

Ser Thr Ile Gly Pro Met Leu Val Asp Ala Phe Lys Asn Leu Leu Ala
                245                 250                 255

Val Ser Val Ala Thr Ser Tyr Glu Phe Glu Glu His Asn Gly Lys Glu
                260                 265                 270

Leu Arg Glu Ala Ala Ile Asn Gly Leu Leu Ala Gly Ser Gly Ser Ala
            275                 280                 285
```

```
Ala Ala Glu Pro Ala Ala Ala Pro Ala Ala Pro Ser Ala Ala Ala
    290                 295                 300
Lys Glu Glu Pro Glu Glu Ser Asp Glu Asp Phe Gly Met Gly Gly
305                 310                 315                 320
Leu Phe
```

(2) INFORMATION FOR SEQ ID NO:3:

(i) SEQUENCE CHARACTERISTICS:
        (A) LENGTH: 955 amino acids
        (B) TYPE: amino acid
        (C) STRANDEDNESS:
        (D) TOPOLOGY: linear (xi) SEQUENCE DESCRIPTION: SEQ ID NO:3:

```
Met His Pro Ser Thr Val Arg Arg Glu Ala Glu Arg Val Lys Val Ser
1               5                   10                  15
Val Arg Val Arg Pro Leu Asn Glu Arg Glu Asn Asn Ala Pro Glu Gly
                20                  25                  30
Thr Lys Val Thr Val Ala Ala Lys Gln Ala Ala Val Val Thr Val
            35                  40                  45
Lys Val Leu Gly Gly Ser Asn Asn Ser Gly Ala Ala Glu Ser Met Gly
50                  55                  60
Thr Ala Arg Arg Val Ala Gln Asp Phe Gln Phe Asp His Val Phe Trp
65                  70                  75                  80
Ser Val Glu Thr Pro Asp Ala Cys Gly Ala Thr Pro Ala Thr Gln Ala
                85                  90                  95
Asp Val Phe Arg Thr Ile Gly Tyr Pro Leu Val Gln His Ala Phe Asp
                100                 105                 110
Gly Phe Asn Ser Cys Leu Phe Ala Tyr Gly Gln Thr Gly Ser Gly Lys
            115                 120                 125
Thr Tyr Thr Met Met Gly Ala Asp Val Ser Ala Leu Ser Gly Glu Gly
130                 135                 140
Asn Gly Val Thr Pro Arg Ile Cys Leu Glu Ile Phe Ala Arg Lys Ala
145                 150                 155                 160
Ser Val Glu Ala Gln Gly His Ser Arg Trp Ile Val Glu Leu Gly Tyr
                165                 170                 175
Val Glu Val Tyr Asn Glu Arg Val Ser Asp Leu Leu Gly Lys Arg Lys
                180                 185                 190
Lys Gly Val Lys Gly Gly Glu Val Tyr Val Asp Val Arg Glu
            195                 200                 205
His Pro Ser Arg Gly Val Phe Leu Glu Gly Gln Arg Leu Val Glu Val
        210                 215                 220
Gly Ser Leu Asp Asp Val Val Arg Leu Ile Glu Ile Gly Asn Gly Val
225                 230                 235                 240
Arg His Thr Ala Ser Thr Lys Met Asn Asp Arg Ser Arg Ser His
                245                 250                 255
Ala Ile Ile Met Leu Leu Leu Arg Glu Glu Arg Thr Met Thr Thr Lys
                260                 265                 270
Ser Gly Glu Thr Ile Arg Thr Ala Gly Lys Ser Ser Arg Met Asn Leu
            275                 280                 285
Val Asp Leu Ala Gly Ser Glu Arg Val Ala Gln Ser Gln Val Glu Gly
        290                 295                 300
Gln Gln Phe Lys Glu Ala Thr His Ile Asn Leu Ser Leu Thr Thr Leu
305                 310                 315                 320
```

-continued

```
Gly Arg Val Ile Asp Val Leu Ala Asp Met Ala Thr Lys Gly Ala Lys
            325                 330                 335

Ala Gln Tyr Ser Val Ala Pro Phe Arg Asp Ser Lys Leu Thr Phe Ile
            340                 345                 350

Leu Lys Asp Ser Leu Gly Gly Asn Ser Lys Thr Phe Met Ile Ala Thr
            355                 360                 365

Val Ser Pro Ser Ala Leu Asn Tyr Glu Glu Thr Leu Ser Thr Leu Arg
370                 375                 380

Tyr Ala Ser Arg Ala Arg Asp Ile Val Asn Val Ala Gln Val Asn Glu
385                 390                 395                 400

Asp Pro Arg Ala Arg Ile Arg Glu Leu Glu Gln Met Glu Asp
                405                 410                 415

Met Arg Gln Ala Met Ala Gly Gly Asp Pro Ala Tyr Val Ser Glu Leu
            420                 425                 430

Lys Lys Lys Leu Ala Leu Leu Glu Ser Glu Ala Gln Lys Arg Ala Ala
            435                 440                 445

Asp Leu Gln Ala Leu Glu Arg Glu Arg Glu His Asn Gln Val Gln Glu
            450                 455                 460

Arg Leu Leu Arg Ala Thr Glu Ala Glu Lys Ser Glu Leu Glu Ser Arg
465                 470                 475                 480

Ala Ala Ala Leu Gln Glu Glu Met Thr Ala Thr Arg Arg Gln Ala Asp
            485                 490                 495

Lys Met Gln Ala Leu Asn Leu Arg Leu Lys Glu Gln Ala Arg Lys
            500                 505                 510

Glu Arg Glu Leu Leu Lys Glu Met Ala Lys Lys Asp Ala Ala Leu Ser
            515                 520                 525

Lys Val Arg Arg Leu Asp Ala Glu Ile Ala Ser Glu Arg Glu Lys
            530                 535                 540

Leu Glu Ser Thr Val Ala Gln Leu Glu Arg Glu Gln Arg Glu Arg Glu
545                 550                 555                 560

Val Ala Leu Asp Ala Leu Gln Thr His Gln Arg Lys Leu Gln Glu Ala
            565                 570                 575

Leu Glu Ser Ser Glu Arg Thr Ala Ala Glu Arg Asp Gln Leu Leu Gln
            580                 585                 590

Gln Leu Thr Glu Leu Gln Ser Glu Arg Thr Gln Leu Ser Gln Val Val
            595                 600                 605

Thr Asp Arg Glu Arg Leu Thr Arg Asp Leu Gln Arg Ile Gln Tyr Glu
610                 615                 620

Tyr Gly Glu Thr Glu Leu Ala Arg Asp Val Ala Leu Cys Ala Ala Gln
625                 630                 635                 640

Glu Met Glu Ala Arg Tyr His Ala Ala Val Phe His Leu Gln Thr Leu
            645                 650                 655

Leu Glu Leu Ala Thr Glu Trp Glu Asp Ala Leu Arg Glu Arg Ala Leu
            660                 665                 670

Ala Glu Arg Asp Glu Ala Ala Ala Glu Leu Asp Ala Ala Ser
            675                 680                 685

Thr Ser Gln Asn Ala Arg Glu Ser Ala Cys Glu Arg Leu Thr Ser Leu
            690                 695                 700

Glu Gln Gln Leu Arg Glu Ser Glu Glu Arg Ala Ala Glu Leu Ala Ser
705                 710                 715                 720

Gln Leu Glu Ala Thr Ala Ala Lys Ser Ser Ala Glu Gln Asp Arg
            725                 730                 735

Glu Asn Thr Arg Ala Thr Leu Glu Gln Gln Leu Arg Glu Ser Glu Ala
            740                 745                 750
```

```
Arg Ala Ala Glu Leu Ala Ser Gln Leu Glu Ala Thr Ala Ala Lys
            755                 760                 765

Met Ser Ala Glu Gln Asp Arg Glu Asn Thr Arg Ala Thr Leu Glu Gln
    770                 775                 780

Gln Leu Arg Asp Ser Glu Arg Ala Ala Glu Leu Ala Ser Gln Leu
785                 790                 795                 800

Glu Ser Thr Thr Ala Ala Lys Met Ser Ala Glu Gln Asp Arg Glu Ser
                805                 810                 815

Thr Arg Ala Thr Leu Glu Gln Gln Leu Arg Asp Ser Glu Glu Arg Ala
            820                 825                 830

Ala Glu Leu Ala Ser Gln Leu Glu Ser Thr Thr Ala Ala Lys Met Ser
            835                 840                 845

Ala Glu Gln Asp Arg Glu Ser Thr Arg Ala Thr Leu Glu Gln Gln Leu
    850                 855                 860

Arg Glu Ser Glu Glu Arg Ala Ala Glu Leu Ala Ser Gln Leu Glu Ser
865                 870                 875                 880

Thr Thr Ala Ala Lys Met Ser Ala Glu Gln Asp Arg Glu Ser Thr Arg
                885                 890                 895

Ala Thr Leu Glu Gln Gln Leu Arg Asp Ser Glu Glu Arg Ala Ala Glu
            900                 905                 910

Leu Ala Ser Gln Leu Glu Ala Thr Ala Ala Lys Ser Ser Ala Glu
            915                 920                 925

Gln Asp Arg Glu Asn Thr Arg Ala Ala Leu Glu Gln Gln Leu Arg Asp
930                 935                 940

Ser Glu Glu Arg Ala Ala Glu Leu Ala Ser Gln
945                 950                 955

(2) INFORMATION FOR SEQ ID NO:4:

(i) SEQUENCE CHARACTERISTICS:
        (A) LENGTH: 3319 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO:4:

GCTCCCACGG CGCTACCCCC TTTCCCGCAT GTGCGACAGT TTCACGCGTA CAAACGTCTT      60

TCTCTCTCCT TCGCGCGTGT CGCTATGGGC GGCGGCGCGT CGGTGTCTTT GATTGCACAG     120

CTCACCGCCT CGCCATATTT TCGTCGTGGC CACGCGACCC CCCGACCTTC CCCTCCTCCG     180

CCCCCAAAGA CAAGCCAGAC ATACCGACCA TGCCGTCTGC CCGCGTCTCT GCTTACCAAG     240

CGCGCCACGC ACCCCTTCCT CGGCCCTGAA TCTTTCGCGC GGCGCCATAC ATTGCATGCA     300

CGTCACTACG CCTGTACACC TTACACCTCC TCTTGCCCAC CCCTTTCCCC TTCTACACGC     360

CTAACTACAC ACACATATAT ATATATATAT ATAAAGCGCT CAACGCACAC ATACTGTGGC     420

CAGTATTACT GCACCAACGT CTGCCTCTTC CAGGATGCAC CCTTCCACTG TGCGGCGTGA     480

GGCGGAGCGG GTGAAGGTGT CGGTGCGCGT GCGCCCCCTA AACGAACGTG AAAACAATGC     540

CCCGGAAGGG ACGAAAGTGA CCGTTGCGGC GAAACAGGCG GCCGCCGTGG TGACGGTCAA     600

GGTCCTGGGA GGCAGCAACA ACAGCGGCGC CGCCGAGTCG ATGGGGACTG CAAGGCGGGT     660

AGCGCAGGAC TTTCAGTTCG ACCACGTGTT CTGGTCTGTG GAGACGCCGG ACGCGTGCGG     720

CGCGACCCCC GCGACGCAGG CAGACGTGTT CCGGACGATC GGGTACCCGC TGGTGCAGCA     780

CGCGTTCGAC GGGTTCAACT CGTGCTTGTT TGCGTACGGG CAGACAGGGA GCGGGAAGAC     840
```

```
GTACACGATG ATGGGCGCGG ACGTGAGCGC GCTTAGTGGT GAGGGCAACG GCGTGACGCC      900

GCGGATCTGC CTGGAGATCT TTGCGCGGAA GGCGAGCGTG GAGGCGCAGG GGCACTCGCG      960

GTGGATCGTG GAGCTGGGGT ACGTGGAGGT GTACAACGAG CGCGTGTCGG ACCTGCTTGG     1020

GAAGCGGAAG AAGGGTGTGA AGGGCGGCGG CGAGGAGGTG TACGTGGACG TGCGCGAGCA     1080

CCCGAGCCGC GGCGTGTTCC TGGAGGGGCA GCGGCTGGTG GAGGTTGGGA GCCTGGACGA     1140

TGTTGTGCGG CTGATCGAGA TCGGCAACGG CGTGCGGCAC ACCGCTTCGA CGAAGATGAA     1200

CGACCGGAGC AGCGGAGCC ACGCGATCAT CATGCTGCTG CTGCGCGAGG AGCGGACGAT     1260

GACGACGAAG AGCGGGGAGA CGATCCGTAC TGCCGGCAAG AGCAGCCGCA TGAACCTTGT     1320

GGACCTTGCG GGGTCTGAGC GCGTGGCGCA GTCGCAGGTG GAGGGGCAGC AGTTCAAGGA     1380

GGCGACGCAC ATCAACCTGT CGCTGACGAC GCTCGGGCGC GTGATCGACG TGCTCGCGGA     1440

CATGGCGACG AAGGGTGCGA AGGCGCAGTA CAGCGTTGCG CCGTTCCGCG ACTCGAAGCT     1500

GACGTTCATC CTGAAGGACT CGCTTGGCGG GAACTCGAAG ACGTTCATGA TCGCGACTGT     1560

GAGCCCGAGC GCGCTGAACT ACGAGGAGAC GCTGAGCACG CTGCGGTACG CGTCGCGCGC     1620

GCGCGACATT GTGAATGTTG CGCAGGTGAA CGAGGACCCG CGCGCACGGC GGATCCGCGA     1680

GCTGGAGGAG CAGATGGAGG ACATGCGGCA GGCGATGGCT GGCGGCGACC CCGCGTACGT     1740

GTCTGAGCTG AAGAAGAAGC TTGCGCTGCT GGAGTCGGAG GCGCAGAAGC GTGCGGCGGA     1800

CCTGCAGGCG CTGGAGAGGG AGCGGGAGCA CAACCAGGTG CAGGAGCGGC TGCTGCGCGC     1860

GACGGAGGCG GAGAAGAGCG AGCTGGAGTC GCGTGCGGCT GCGCTGCAGG AGGAGATGAC     1920

CGCGACTCGA CGGCAGGCGG ACAAGATGCA GGCGCTGAAC CTGCGGCTGA AGGAAGAGCA     1980

GGCGCGCAAG GAGCGCGAGC TGCTGAAAGA GATGGCGAAG AAGGACGCCG CGCTCTCGAA     2040

GGTTCGGCGA CGCAAAGACG CCGAGATAGC AAGCGAGCGC GAGAAGCTGG AGTCGACCGT     2100

GGCGCAGCTG GAGCGTGAGC AGCGCGAGCG CGAGGTGGCT CTGGACGCAT TGCAGACGCA     2160

CCAGAGAAAG CTGCAGGAAG CGCTCGAGAG CTCTGAGCGG ACAGCCGCGG AAAGGGACCA     2220

GCTGCTGCAG CAGCTAACAG AGCTTCAGTC TGAGCGTACG CAGCTATCAC AGGTTGTGAC     2280

CGACCGCGAG CGGCTTACAC GCGACTTGCA GCGTATTCAG TACGAGTACG GGAAACCGA     2340

GCTCGCGCGA GACGTGGCGC TGTGCGCCGC GCAGGAGATG GAGGCGCGCT ACCACGCTGC     2400

TGTGTTTCAC CTGCAAACGC TCCTGGAGCT CGCAACCGAG TGGGAGGACG CACTCCGCGA     2460

GCGTGCGCTT GCAGAGCGTG ACGAAGCCGC TGCAGCCGAA CTTGATGCCG CAGCCTCTAC     2520

TTCCCAAAAC GCACGTGAAA GCGCCTGCGA GCGGCTAACC AGCCTTGAGC AGCAGCTTCG     2580

CGAATCCGAG GAGCGCGCTG CGGAGCTGGC GAGCCAGCTG GAGGCCACTG CTGCTGCGAA     2640

GTCGTCGGCG GAGCAGGACC GCGAGAACAC GAGGGCCACG CTAGAGCAGC AGCTTCGCGA     2700

ATCCGAGGCG CGCGCTGCGG AGCTGGCGAG CCAGCTGGAG GCCACTGCTG CTGCGAAGAT     2760

GTCAGCGGAG CAGGACCGCG AGAACACGAG GGCCACGCTA GAGCAGCAGC TTCGTGACTC     2820

CGAGGAGCGC GCTGCGGAGC TGGCGAGCCA GCTGGAGTCC ACTACTGCTG CGAAGATGTC     2880

AGCGGAGCAG GACCGCGAGA GCACGAGGGC CACGCTAGAG CAGCAGCTTC GTGACTCCGA     2940

GGAGCGCGCT GCGGAGCTGG CGAGCCAGCT GGAGTCCACT ACTGCTGCGA AGATGTCAGC     3000

GGAGCAGGAC CGCGAGAGCA CGAGGGCCAC GCTAGAGCAG CAGCTTCGCG AATCCGAGGA     3060

GCGCGCTGCG GAGCTGGCGA GCCAGCTGGA GTCCACTACT GCTGCGAAGA TGTCAGCGGA     3120

GCAGGACCGC GAGAGCACGA GGGCCACGCT AGAGCAGCAG CTTCGTGACT CCGAGGAGCG     3180

CGCTGCGGAG CTGGCGAGCC AGCTGGAGGC CACTGCTGCT GCGAAGTCGT CGGCGGAGCA     3240
```

```
GGACCGCGAG AACACGAGGG CCGCGTTGGA GCAGCAGCTT CGTGACTCCG AGGAGCGCGC    3300

CGCGGAGCTG GCGAGCCAG                                                3319
```

(2) INFORMATION FOR SEQ ID NO:5:

(i) SEQUENCE CHARACTERISTICS:
        (A) LENGTH: 39 amino acids
        (B) TYPE: amino acid
        (C) STRANDEDNESS:
        (D) TOPOLOGY: linear (ix) FEATURE:
        (A) NAME/KEY: Region
        (B) LOCATION: 7
        (D) OTHER INFORMATION: /note= "The Xaa in position 7 can
            be Asp or Glu"

(ix) FEATURE:
        (A) NAME/KEY: Region
        (B) LOCATION: 10
        (D) OTHER INFORMATION: /note= "Xaa in position 10 can be
            either Glu or Ala"

(ix) FEATURE:
        (A) NAME/KEY: Region
        (B) LOCATION: 21
        (D) OTHER INFORMATION: /note= "The Xaa in position 21 can
            be Ala or Ser"

(ix) FEATURE:
        (A) NAME/KEY: Region
        (B) LOCATION: 23
        (D) OTHER INFORMATION: /note= "The Xaa in position 23 can
            be Ala or Thr"

(ix) FEATURE:
        (A) NAME/KEY: Region
        (B) LOCATION: 27
        (D) OTHER INFORMATION: /note= "The Xaa in position 27 can
            be Met or Ser"

(ix) FEATURE:
        (A) NAME/KEY: Region
        (B) LOCATION: 35
        (D) OTHER INFORMATION: /note= "The Xaa in position 35 can
            be Asn or Ser"

(ix) FEATURE:
        (A) NAME/KEY: Region
        (B) LOCATION: 39
        (D) OTHER INFORMATION: /note= "The Xaa in position 39 can
            be Thr or Ala"

(xi) SEQUENCE DESCRIPTION: SEQ ID NO:5:

```
Leu Glu Gln Gln Leu Arg Xaa Ser Glu Xaa Arg Ala Ala Glu Leu Ala
1               5                   10                  15

Ser Gln Leu Glu Xaa Thr Xaa Ala Ala Lys Xaa Ser Ala Glu Gln Asp
            20                  25                  30

Arg Glu Xaa Thr Arg Ala Xaa
            35
```